(12) United States Patent
Dempers et al.

(10) Patent No.: US 10,950,330 B2
(45) Date of Patent: Mar. 16, 2021

(54) SYSTEM AND METHOD FOR PREDICTIVE AND PREVENTATIVE TREATMENT GUIDANCE FOR SECURE STORAGE ELECTRONIC MEDICAL RECORDS

(71) Applicant: INVARYANT, INC., Roswell, GA (US)

(72) Inventors: Ramon Dempers, Alpharetta, GA (US); Ophir Frieder, Chevy Chase, MD (US)

(73) Assignee: INVARYANT HEALTH LLC, Roswell, GA (US)

( * ) Notice: Subject to any disclaimer, the term of this patent is extended or adjusted under 35 U.S.C. 154(b) by 323 days.

(21) Appl. No.: 16/016,782

(22) Filed: Jun. 25, 2018

(65) Prior Publication Data

US 2018/0308566 A1 Oct. 25, 2018

Related U.S. Application Data

(63) Continuation-in-part of application No. 15/353,993, filed on Nov. 17, 2016, now abandoned.
(Continued)

(51) Int. Cl.
| | |
|---|---|
| *G06Q 50/00* | (2012.01) |
| *G16H 10/60* | (2018.01) |
| *G06F 21/62* | (2013.01) |
| *H04L 9/06* | (2006.01) |
| *G06F 16/23* | (2019.01) |

(Continued)

(52) U.S. Cl.
CPC ............ *G16H 10/60* (2018.01); *G06F 16/23* (2019.01); *G06F 16/27* (2019.01); *G06F 21/35* (2013.01); *G06F 21/6245* (2013.01); *H04L 9/0637* (2013.01); *H04L 9/0894* (2013.01); *H04L 9/12* (2013.01); *H04L 9/3236* (2013.01); *H04L 63/0853* (2013.01); *H04L 2209/38* (2013.01); *H04L 2209/88* (2013.01)

(58) Field of Classification Search
None
See application file for complete search history.

(56) References Cited

U.S. PATENT DOCUMENTS

| | | |
|---|---|---|
| 9,716,657 B1 | 7/2017 | Pani et al. |
| 2006/0111943 A1* | 5/2006 | Wu .......................... G06F 19/00 705/3 |

(Continued)

*Primary Examiner* — Jonathan Ng
(74) *Attorney, Agent, or Firm* — Pauley Erickson & Swanson

(57) ABSTRACT

A system and method that facilitates the automated replication of electronic medical record information between a patient and a health-care provider (HCP), such as a doctor, pharmacy, drug manufacturer, biologic manufacturer, or medical device manufacturer. The system uses: a cloud-based infrastructure that includes databases, mathematical models, and configuration information; a patient's electronic health record system providing personal data around a patient's individual personal electronic medical record (PEMR); and a server used to coordinate and authenticate the replication of data between the cloud-based infrastructure, the PEMR, and the EMR/EHR system of the HCP. The system provides support and security, such as by geographically distributed data fragmentation, for mobile platforms and web-based platforms and sophisticated mechanisms for the transmission of data between these systems.

22 Claims, 30 Drawing Sheets

Related U.S. Application Data

(60) Provisional application No. 62/525,862, filed on Jun. 28, 2017, provisional application No. 62/370,068, filed on Aug. 2, 2016.

(51) Int. Cl.
| | |
|---|---|
| *G06F 16/27* | (2019.01) |
| *H04L 9/08* | (2006.01) |
| *H04L 9/32* | (2006.01) |
| *G06F 21/35* | (2013.01) |
| *H04L 9/12* | (2006.01) |
| *H04L 29/06* | (2006.01) |

(56) References Cited

U.S. PATENT DOCUMENTS

| | | | |
|---|---|---|---|
| 2012/0129139 A1* | 5/2012 | Partovi | G16H 10/60 434/262 |
| 2013/0054271 A1 | 2/2013 | Langford et al. | |
| 2014/0142979 A1* | 5/2014 | Mitsunaga | G06Q 50/24 705/3 |
| 2014/0207686 A1 | 7/2014 | Experton | |
| 2014/0316812 A1* | 10/2014 | Hathorn | G16H 10/60 705/3 |
| 2015/0193183 A1 | 7/2015 | Ichikawa et al. | |
| 2015/0312243 A1* | 10/2015 | Ponsford | G06F 21/6218 713/159 |
| 2016/0132684 A1* | 5/2016 | Barbas | G06F 3/067 713/165 |
| 2017/0161439 A1* | 6/2017 | Raduchel | G06F 16/24578 |
| 2017/0364698 A1* | 12/2017 | Goldfarb | G06F 16/9024 |
| 2018/0039737 A1 | 2/2018 | Dempers et al. | |

\* cited by examiner

901

SYSTEM AND METHOD FOR PREDICTIVE AND PREVENTATIVE TREATMENT GUIDANCE FOR SECURE STORAGE ELECTRONIC MEDICAL RECORDS

CROSS REFERENCE TO RELATED APPLICATION

This application: is a continuation-in-part of U.S. patent application Ser. No. 15/353,993, filed on 17 Nov. 2016, which claims the benefit of U.S. Provisional Patent Application Ser. No. 62/370,068, filed on 2 Aug. 2016; and also claims the benefit of U.S. Provisional Patent Application Ser. No. 62/525,862, filed on 28 Jun. 2017. The co-pending parent and provisional applications are hereby incorporated by reference herein in its entirety and is made a part hereof, including but not limited to those portions which specifically appear hereinafter.

BACKGROUND

This invention is directed to consolidating and synchronizing medical history, and more particularly to a method and system for data synchronization of centralized patient health data with remote health-care providers.

The health-care industry has made a nearly complete shift to utilizing electronic health records (EHRs), alternatively referred to herein as electronic medical records (EMRs). However, the data in these records are typically stored in silos. That is, typically each health-care provider (HCP) maintains a unique patient database organized frequently using a unique EMR software. Accordingly, the data are fragmented between different HCPs and are never consolidated, neither physically nor logically, in a single data structure. Additionally, patients have information about lifestyle and life choices that is not recorded. More so, other HCPs, such as, but not limited to, dentists, optometrists, psychologists, nutritionists, physical therapists, and clinicians providing basic medical care in pharmacies, have relevant data but are largely likewise ignored by HCPs. Furthermore, inevitably, a patient, during their lifetime, will have unexpected visits to emergency medical facilities or hospital emergency rooms (ERs) for emergent situations that will generate further data that reside in yet another medical record silo. Finally, care is likewise provided through technology platforms such as telemedicine, coordinated care, and insurance company outlets and in "mini-clinics" in pharmacies and grocery stores. The medical market will continue to fragment; concierge medicine, in various forms, will further emerge; providing a new and growing segment of in-home medical care. Consequently, the patient's medical records are becoming ever more fragmented, and the risks to both patient and provider are exacerbated.

Despite advances in the integration of patient medical data, patient data remains largely contained in disparate medical data silos. Moreover, patients are at significant medical risk due to the lack of integration presently available for patient's EMRs. A further issue is that the data remain bound to HCPs and are not centered upon or controlled by the patient. These needs and others are addressed by the present disclosure.

SUMMARY OF THE INVENTION

The present invention, as embodied and broadly described herein, relates to the consolidation and synchronization of patient medical information in a single, logical, patient-controlled EMR. In embodiments of this invention each EMR is referred to as an "invaryant" and is a holistic record including vital health and life data about a person's health and/or life experience, captured in a single, accessible format. Such a record includes but is not limited to entries specifying medical conditions and treatments; proteomic, genomic, and microbiome indicators; life style data, related socio-economic indicators; nutrition; fitness; sleep patterns; socio-economic conditions; and/or environmental conditions. Storing, modeling, and analyzing such holistic records so as to manage and manipulate symptoms, conditions, and treatments demands efficient, scalable, and adaptive systems.

Even if integrated, current EMRs (e.g., U.S. Pat. No. 9,305,140) fail to capture the state of being of an individual, namely, the daily functioning of the individual outside of the traditional medical space is mostly neglected if not fully ignored. Environmental, nutritional, behavioral and other elements all affect the physical and psychological state of the patient; yet, traditional EMRs forgo this critical information. Embodiments of this invention include these as well as other related information in the patient invaryant EHR/EMR, such as data generated from wearable technology, smartphones and other Internet of Things devices. Conceptually, an invaryant EMR is a holistic life-long history of any condition including but not limited to physical, psychological, social, and environmental, that impact an individual's life.

Another issue addressed in the present invention is the lack of a life-long historical characterization and information collection of an individual's patient history. Without such a history, it is difficult, if not impossible, to compute a complete analysis of a patient's health status. Furthermore, having life-long historical characterizations of a large population, health insight both for a group and for an individual can be derived. A data lake of individual 'invaryants' is disclosed herein to support knowledge generation.

Yet another issue is the treatment of the state of health of an individual as a circuit consisting of feedback and propagation of conditions. That is, each body system is influenced by and influences the remaining body systems. Monitoring the state of this circuit enables the detection of emerging pre-conditions for disease likelihood, onset, and development. Treatment effects as well as other external-factor influences are observable. Embodiments of this invention address this issue via the use of, for example, neural gateways.

It is within the scope of this invention that the patient EMR be distributed physically but be logically viewed as one record. In embodiments of this invention, the system of consolidation is designed to be simple, be comprehensive, and place minimal burden, or significantly reduced burden, on the patient, health-care provider (HCP), and other entities involved in the health and care of the patient. In some embodiments, the system provides controls and mathematical models to promote patient safety, both actively and via trending signals in the data, while reducing the risk for HCPs, who are empowered with a full view of the medical condition of their patient rather than with only the patient's current state, which relies heavily on patient-provided information and that health-care provider's (HCP's) EMRs. Implementation of such a system, without loss of generality, uses secure chained, engineered fragmented data storage, and/or processing via body system specific neural gateways, teaching some and controlling other neural gateways.

The invention provides a system for consolidating and synchronizing medical history for a patient. Embodiments of the system include: a personal electronic medical record (EMR) for the patient, stored in a database on a non-volatile memory device, an authenticator assigned to the patient to allow access to the personal electronic medical record, and a remote server apparatus configured to issue or receive the authenticator and authorize access to the personal medical health record by a health-care provider server apparatus. The personal EMR can include, without limitation, patient diagnoses, medications, details of acute, chronic and terminal illness, medical history, family medical history, laboratory test results, imaging records, and combinations thereof. The remote server apparatus desirably issues the authenticator to a patient electronic device and receives the authenticator from a provider authenticating device in combination with the health-care provider server apparatus, over a network, and then synchronizes the patient EMR and the provider's EMR for the patient.

In embodiments of this invention, the authenticator is obtained by the health-care provider server apparatus from the patient and automatically transmitted to the remote server apparatus to authorize the access to the personal electronic medical record. The authenticator is preferably obtained/transferred using a computer-readable indicia, such as, for example, a PIN, a QR code, NFC token, or RFID, that can be read or otherwise transferred from the patient (e.g., via a patient mobile device) to a health-care provider (e.g., via a scanner or receiver) upon the patient's arrival at the health-care provider. In one embodiment of this invention, the authenticator comprises an encrypted token adapted to be passed from a patient electronic device to the health-care provider server apparatus, and from the health-care provider server apparatus to the remote server apparatus to access the EHR. The patient electronic device disconnects from the health-care provider authentication device and/or server apparatus upon passing the authenticator, so that data from or to the personal EMR data automatically transfers from or to the health-care provider server apparatus via the remote server apparatus and not through the patient electronic device.

The invention further includes a system for consolidating and synchronizing medical history for a patient that includes a personal electronic medical record (PEMR) for the patient and stored in a database on a non-volatile memory device in combination with a patient electronic medical record server. An authenticator assigned to the patient allows access, such as by a health-care provider 'given' the authenticator, to the personal electronic medical record. An access module that is executable on a health-care provider server apparatus receives the authenticator as a patient sign-in upon patient arrival at and/or departure from a health-care facility of the health-care provider server apparatus. A remote server apparatus is configured to issue the authenticator to the patient through a patient electronic device, to receive the authenticator from the health-care provider server apparatus, and to authorize transfer of, replication of, and/or updating of the PEMR by the health-care facility. The patient electronic medical record server can include a data synchronization module configured to communicate with and synchronize patient data, such as via the remote server apparatus, with a health-care provider database in combination with the health-care provider server apparatus. The authenticator can be received by the health-care provider server apparatus from the patient electronic device and automatically transmitted to the remote server apparatus to authorize the access to the personal electronic medical record.

The invention further provides a method for consolidating and synchronizing medical history for a patient. The method includes: storing a personal electronic medical record for the patient in a database on a non-volatile memory device in combination with a patient electronic medical record server; automatically issuing an authenticator to the patient by a remote server apparatus to allow access to the personal electronic medical record, wherein the patient uses the authenticator as a patient sign-in at a health-care facility; automatically receiving the authenticator from a health-care provider server apparatus as the patient sign-in upon patient arrival at and/or departure from the health-care facility; and automatically authorizing transfer of, replication of, and/or updating of the personal electronic medical record by the health-care facility upon receipt of the authenticator.

The invention further provides method of securely consolidating and synchronizing medical history for a patient by automatically fragmenting a personal electronic medical record (PEMR) for the patient into a plurality of data fragments; storing the plurality of data fragments distributed across one or more databases; reassembling the plurality of data fragments for display of the personal electronic medical record via a computer system of a health-care provider; updating the personal electronic medical record with data from the health-care provider to form an updated personal electronic medical record for the patient; and automatically fragmenting the updated personal electronic medical record for the patient into a second plurality of data fragments for storage across the one or more databases. Desirably no integrated copy of the personal electronic medical record is stored on the one or more databases. The reassembling of the PEMR only occurs during active treatment of the patient by the health-care provider. In embodiments of this invention, no copy of the PEMR or the updated PEMR remains on any user component of the computer system of the health care provider upon closing the updated personal electronic medical record.

Embodiments of the invention include randomly distributing the data fragments across the one or more databases. In embodiments of the invention, the data fragments are distributed across a plurality of geographically distributed databases. A sequence generator can be automatically attached to each of the plurality of data fragments and the second plurality of data fragments for reassembling. A block chain code can be used to authenticate the data fragments and sequence for reassembling. In addition, the information in the PEMR can be categorized and/or prioritized during or upon reassembling for display of relevant health information as a function of a specialty or interest of the health-care provider.

The method further includes a method of consolidating and synchronizing medical history for a patient including: automatically fragmenting a personal electronic medical record for the patient into a plurality of data fragments, via a cloud based data server; the cloud based data server storing the plurality of data fragments as a plurality of distributed data fragment objects; receiving a request for the personal electronic medical record by a first health-care provider treating the patient; automatically synchronizing the distributed data fragment objects in a local electronic medical record of the health-care provider; transferring an updated personal electronic medical record from the first health-care provider to the cloud based data server; automatically fragmenting the updated personal electronic medical record for the patient into a second plurality of data fragments, via the cloud based data server; and the cloud based data server storing the plurality of data fragments as a second plurality of distributed data fragment objects until requested by the first health-care provider or a second health-care provider.

The method can further include: receiving a second request for the personal electronic medical record by the second health-care provider treating the patient; automatically synchronizing the distributed second plurality of data fragment objects in a second local electronic medical record of the second health-care provider; and transferring a further updated personal electronic medical record from the second health-care provider to the cloud based data server for distributed storage. The method desirably includes automatically synchronization of the local electronic medical record of the first health-care provider with the updated personal electronic medical record upon receiving a further request for the personal electronic medical record by the first health-care provider. In actual implementation, the method will generally be applied to a plurality of personal electronic medical records, and further include: automatically fragmenting each of the personal electronic medical records into the plurality of data fragments, via the cloud based data server; and distributing the data fragments across a plurality of geographically distributed databases. The data fragments for the each of the personal electronic medical records are desirably distributed across at least two different combinations of the geographically distributed databases.

The invention further includes a system for consolidating and synchronizing medical history for a patient. The system includes a personal electronic medical record for the patient, stored as data fragments in a distributed database on a non-volatile memory device; an authenticator assigned to the patient to allow access to the personal electronic medical record; and a remote server apparatus configured to issue or receive the authenticator and authorize synchronization of the fragments of the personal electronic medical record by or on a local electronic medical record on a health-care provider server. The distributed database desirably includes a block chain database, and the authenticator includes a block chain code that authenticates the data fragments and a corresponding sequence for synchronization.

While aspects of the present disclosure can be described and claimed in a particular statutory class, such as the system statutory class, this is for convenience only, and one of skill in the art will understand that each embodiment of the present disclosure can be implemented and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several embodiments and, together with the description, serve to explain the principles of the present disclosure.

Figure 1:
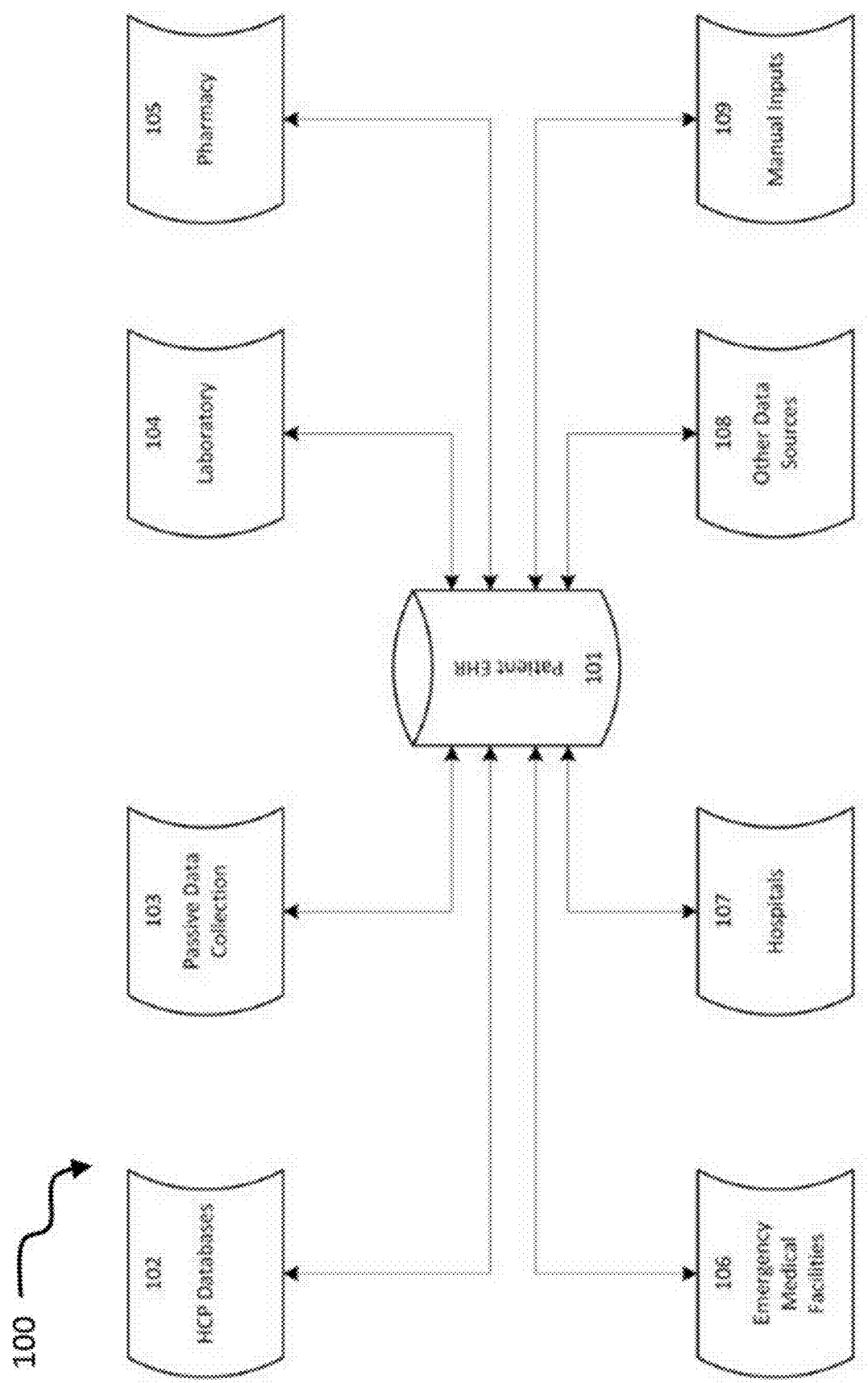
FIG. 1 shows a representative embodiment of representative data sources for synchronization. Additional data sources not shown are also within the scope of the present invention.

Additional advantages of the disclosure will be set forth in part in the description that follows and in part will be obvious from the description or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DESCRIPTION OF EMBODIMENTS OF THE INVENTION

The present disclosure can be understood more readily by reference to the following detailed description of the disclosure.

As used in the specification and the appended claims, the singular forms "a," "an," and "the" include plural referents unless the context clearly dictates otherwise. Thus, for example, reference to "a health record"; "an algorithm"; or "a QR code," "RFID," or "PIN" includes mixtures of two or more such functional health records; algorithms; QR codes, RFIDs, or PINs; and the like.

Ranges can be expressed herein as from "about" one particular value and/or to "about" another particular value. When such a range is expressed, a further aspect includes from the one particular value and/or to the other particular value. Similarly, when values are expressed as approximations by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" mean that the subsequently described event or circumstance can or cannot occur, and that the description includes instances where the event or circumstance occurs and instances where it does not.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including the following: matters of logic with respect to arrangement of steps or operational flow, plain meaning derived from grammatical organization or punctuation, and the number or type of aspects described in the specification.

As described above, currently, data in patient's EHRs, alternatively referred to as electronic medical records (EMRs), exist in multiple data silos. Thus, critical patient data are often fragmented between different health-care providers (HCPs) and are never consolidated in a logical and/or physical single data structure. The data siloing of patient information exists among the various providers a patient normally sees, such as their primary care physician (PCP) and specialists to whom they are referred. Additionally, patients have information about their lifestyle, life choices, and self-prescribed herbal supplements, vitamins, and other medications. Other HCPs, such as, but not limited to, dentists, optometrists, psychologists, nutritionists, physical therapists, Eastern medicine doctors, and clinicians providing basic medical care in pharmacies, likewise have relevant data. Even further yet, a patient, during their lifetime, will have unexpected visits to an emergency medical facilities or hospital ERs for emergency situations, which generate further data that reside in a medical record silo.

Despite the shift to utilizing EHRs, or EMRs, HCPs largely ignore the above relevant data. Centers for Disease Control (CDC) statistics state that there are approximately 1,000 deaths and 10,000 serious injuries daily in the United States as a result of medical errors related to incorrect, unavailable, or missing data. Moreover, reports from the Food and Drug Administration (FDA) and the National Institutes of Health (NIH) place the estimate of unreported adverse events (AEs) and serious adverse events (SAEs) to be as high as 75 million cases per year.

The fragmentation of patient information, i.e., the siloing of EHR/EMR information, means that HCPs and other health-care organizations are limited in being able to understand or correct procedures leading to patient adverse events (AEs). Currently, AEs experienced in both post-market surveillance and, to a lesser extent, in clinical trials are reported at the next patient visit to the prescribing HCP. However, for example, what often occurs is that the patient stops taking the medication and never reports the AE to their HCP, or their next visit to the physician is weeks, months, a year, or more away. Patient safety is put at risk through non-adherence, and the burden on the health system in the United States is estimated to be up to $289 billion dollars in direct costs based on various CDC and World Health Organization (WHO) sources. Additionally, the percentage of medication prescriptions that are not filled is as high as 30% of all scripts issued. For those scripts filled, the medication is incorrectly used or stopped 50% of the time; rates of adherence drop after the first six months, and non-adherence results in 125,000 deaths annually.

Regardless of the reason for this fragmented information spread across multiple databases, whether it is a result of regular visitations or emergencies, the situation puts patients and their HCPs at grave risk. In the case of the patient, there can be significant, even life threatening, risks, and in the case of the HCP, the risks are associated with a lack of or gaps in their knowledge about the patient they are treating, and as a result, they are placed in a position of having to make an "educated guess." More so, computerized diagnostics is increasing in prevalence, but proper capitalization on such diagnostic tools is reduced as the relevant data are siloed. Society must tackle and meet this breakdown in the health-care system to protect patients and provide them with more precise, consolidated, and data-driven care.

A further serious clinical issue arising from fragmented or siloed data is that patients find they undergo repeated testing, such as laboratory or imaging tests, which can and often does lead to additional serious side effects for the patient. There are also significant cost implications for repeatedly running the same or similar tests on a patient. Some estimates indicate that this expense is as high as one quarter of the national health-care expenditure, or six hundred and sixty billion dollars. Additionally, in terms of patient care, siloed test results complicate, if not outright impede, longitudinal analysis of patient condition, reducing the diagnosis ability and treatment quality.

While the government, industry, and other entities are trying to find solutions for above-described fragmentation of medical data for patients, current approaches are directed at the databases themselves and the integration of those databases from facility to facility, either through direct connectivity or via state-based exchanges. This approach is cumbersome, requires a remarkable level of coordination among disparate entities, and leaves the data outside the control of the patient. Moreover, the technologies rapidly evolve and change, and maintaining this connectivity and synchronization, despite efforts of building standards, has been largely unsuccessful.

Specifically, patient control of data is critical. Throughout their lives, patients likely will relocate, at least temporarily, and hence, data mobility should follow. More so, patients may wish to transfer HCPs for cost, convenience, or other reasons; pursue other modes of health care for need, conviction, or other reasons; or simply request guidance from other means. Hence, solutions that support patient control of data must be developed.

In the case of the state exchanges, the interoperability applies only to the state where the patient lives. Thus, should a patient need to leave the state for medical care, or require medical care as a result of travel out of state, their medical record will not be available via the state-based exchange of the state in which they reside. An additional concern for a patient is that their medical information is under the control of a state organization and is being transmitted from a state-based exchange. This approach presents risks in several areas, including data breaches, unauthorized access to their information, and other risks. Moreover, if there were to be a federal exchange, then this would additionally require that all state exchanges from all states communicate with the federal exchange. This would further exacerbate the risk to an individual patient in terms of the security of their medical information. Additionally, the patient can lose control over who has their information and where it resides. Finally, many of the state-based exchange initiatives, due to the exorbitant cost of maintaining these integrations, fail once federal- or state-based funding is cut or the grant funding ends. The system described herein provides the patient with full control of the medical information and thereby ensures greater confidentiality and security for that patient.

To meet the needs of the consumer when it comes to their health care, two important ideas must be brought to bear on the aforementioned problems: Firstly, the consumer must be placed in a position of power to control their medical destiny, and secondly, they must be the central resource conduit through which all their medical data are maintained and kept current. The reason is simple: The consumer is the only common denominator in the health-care landscape, and a fully empowered consumer will drive the breakdown of the current state of data silos. People who control, understand, and choose to alter their own health path are the new disruptive force in health-care.

In one aspect, the disclosure relates to a system whereby the patient is placed in control of a central EMR, which is then synchronized with other parties, including HCPs, laboratories, pharmacies, drug manufacturers, biologic manufacturers, and medical device manufacturers, amongst others. In various embodiments, the system makes use of current technology platforms in the areas of mobile computing (smartphones, tablets, and laptops), virtual and augmented reality, desktop computing, and/or cloud computing, to describe some of the current platforms. Additionally, the system can make use of future technologies yet to be envisioned where technically appropriate and feasible. In a further embodiment, the system can make use of current and future mathematical models for both responsive and predictive capabilities.

As used herein, the term "mobile device" may comprise a wide variety of computing devices. In some embodiments, the mobile device may refer to a smart phone, a laptop, a tablet, a wearable device, or the like.

As used herein, "readable indicia" may refer to a variety of information types. In some embodiments, readable indicia may refer to a quick response (QR) code, a personal identification number (PIN), radio frequency identification (RFID), a bar code, biometric information, a user identification code, a serial number, a phone number, a text string, an employee identification number (EIN), a tax identification number, or the like. In some embodiments, the readable indicia may include near field communication (NFC) technology and other forms of communication.

As used herein, the term "quick response code," or "QR code," refers to a code that is arranged such that it fulfills the ISO/IEC18004 or similarly focused standard. That is, the code may consist of black modules arranged in a square pattern on a white background. The information encoded can be made up of four standardized modes of data (numeric, alphanumeric, byte/binary, Kanji) or by supported extensions.

In various embodiments, the disclosed system comprises at least three primary components: a) a server that facilitates the data interoperability between the provider's EMR software and the patient's personal electronic health record (PEMR); b) the patient's PEMR, which includes an authentication software client-to-server connector; and c) a PIN generated and sent to the patient by the BUMP Office Server (BOS), a QR scanner, RFID, or NFC components used to identify the patient to the provider's EMR system. In an embodiment, these components plus the patient's mobile platform provide the platform for this system. In some embodiments, and for purposes of description in this disclosure, the aforementioned "server" can be referred to as the "BUMP Office Server," or "BOS."

As used herein, the term "mobile platform" refers to a hardware or software platform used by the patient that is not confined to a single location or software application. "Mobile platform" is inclusive of such devices and interfaces including, but not limited to, smart phone devices; tablet devices; mobile computing devices; virtual reality devices; augmented reality devices; gaming stations; "smart" devices or sensors, including wearable devices or sensors, in-home devices or sensors, and others; or a web browser interface (regardless of the platform hosting the web browser). The mobile platform comprises the "BUMP plugin" software component.

A PEMR server is configured to store the patient's EMR in a remote, secure, and scalable (e.g., cloud-based) platform, and to synchronize a patient's EMR with the HCP's EMR system via a BOS interoperability interface on BOS. The client authenticator software, i.e., the "BUMP plugin" software component, is configured to operate on the mobile platform, and encrypted authentication tokens are passed between the client software on the mobile platform to the HCP's BOS. BOS identifies the patient on the HCP's EMR system, and once the connection is made, BOS initiates the connection to the PEMR cloud-based system. Once the mobile device has confirmed its identity to BOS and the tokens (security codes) are verified on both the HCP's EMR system and the PEMR system, the mobile device is disconnected from the process to ensure greater security during the synchronization of the data. Once the synchronization of the data is complete, BOS transmits a success notification to the HCP's EMR system and potentially displays a detailed transaction description on the BUMP dashboard. It is within the scope of this invention that the patient and/or other designees are notified of this synchronization.

In some embodiments, the authentication code comprises readable indicia. The readable indicia may include, but are not limited to, one or more of the following: a QR code, RFID, NFC, a PIN generated and sent to the patient by BOS, or other similar technology as will occur to one of ordinary skill in the art. In various embodiments, transmitting the authentication code comprises displaying a QR code, RFID, or a PIN on a patient's mobile platform for scanning by the HCP's BOS system scanner. In a further embodiment, transmitting the authentication code comprises scanning of a printed copy of a QR code, RFID, or the entry of a PIN by the HCP's BOS system. Scanning of a QR code, RFID, or entry of the PIN—whether it is displayed on a patient's mobile platform or as a printed copy of the QR code, RFID, or PIN—verifies the patient's arrival at the HCP office and starts the synchronization of the data between the patient's cloud-based PEMR and the provider's EMR. In still further embodiments, upon completion of a patient's appointment, the patient will once again scan the displayed QR code, RFID, or PIN or the printed copy of the QR code, RFID, or PIN to initiate the synchronization of the changes in the patient's medical information on the HCP's EMR system, thereby updating the PEMR via BOS. Importantly, at no time does the mobile device perform any of the data transfer, and it is used only for authentication. BOS shall also maintain and monitor the HCP's EMR for the patient for a period of days, weeks, or any other determined period of time to ensure that any ordered tests (for example, lab tests) that might be returned to the HCP after off-site processing are also synchronized with the patient's record. Before closing the monitoring function, BOS shall send an alert to the patient and the HCP confirming all relevant test information has been received, and upon confirmation, the monitor shall stop. In the event that there are tests that are still underway, the monitoring period will be extended for another period. This process shall repeat until both parties receive confirmation. All transmission shall be encrypted. All interaction will be logged. All transaction dependencies, for example, without loss of generality, follow-ups, and labs, shall be monitored and confirmed as complete.

For example, in some embodiments, the disclosure relates to a system that comprises a patient's personal electronic medical record (PEMR), which is under the control of the patient or an assignee of the patient. Such a health record is used to coordinate and keep current third-party databases, including those of HCPs, laboratories, pharmacies, drug manufacturers, biologic manufacturers, and medical device manufacturers, amongst others. A view of such a system is shown in FIG. 1, in which the components of third-party systems and databases are shown.

In various embodiments, the disclosed system can be used by the patient and third-party entities, including HCPs, laboratories, pharmacies, drug manufacturers, biologic manufacturers, and medical device manufacturers, amongst others, to synchronize and maintain accurate health records for all patients using the system.

In some embodiments, the disclosed system comprises components or devices that can allow a patient and an HCP to agree to the sharing of medical information about the patient prior to execution of the synchronization. Accordingly, HCPs can use disclosure documentation already developed for protecting patient privacy and patient information via electronic confirmation using the system. The system promotes the digital signing of all documents prior to a patient's arrival at the facility, rather than as previously done where the analog documents were signed by the patient upon arrival at the HCP facility. More so, a virtual interaction or evaluation of the HCP and the patient is likewise supported and can rely on the technology to support data synchronization for such interaction.

Accordingly, in various embodiments, HCPs are empowered by a comprehensive 360° view of the patient's medical record, medical history, family medical history, lifestyle, life choices, genetics, and any additional information that promotes health and, where required, accurate diagnosis and treatment of acute, chronic, and terminal conditions based on the aforementioned comprehensive patient data. The benefits to the patient are better health, more accurate diagnoses, and a reduced risk of detrimental drug, biologic, and device interactions. The HCP benefits by basing their diagnosis and treatment on an accurate medical record, rather than on a medical record that is incomplete and/or out of date.

In various embodiments, the disclosed system provides an automated method for integrating the HCP's scheduling software with that of the patient with minimal effort by both the patient and the HCP. The system generates an automated notification from the HCP's scheduling software to the system's BOS, allowing all scheduled visitations to be passed to a scheduling module linked to the patient's EMR system. Additionally, the system sends a notification email and/or text to be sent at a time prior to the scheduled visitation. The system comprises communication modules or devices that can provide identification of a patient with the system's server and further provide a patient with capability to complete several steps prior to their arrival at the HCP's facility. These steps include, but are not limited to, confirming their intention to be present for the visit, agreeing to the synchronization of their medical record—both sending new information to the health-care provider (HCP) and receiving new information from the HCP, and agreeing to the privacy requirements as required by the HCP. In a further embodiment, the HCP is able to balance patient confirmations of attendance and data synchronization and store digitally-signed privacy documentation electronically. The HCP, at their option, may choose or decline to receive medical information from the patient. In a further embodiment, the patient is able to cancel or reschedule their appointment via the PEMR software.

In various embodiments, the disclosed system provides an automated method for synchronizing information using methods that remove the burden of manual data entry by both the patient and the HCP. These methods include the ability of a patient, upon checkout, to confirm the synchronization of their medical record from the HCP based on changes made during the patient visit.

In various embodiments, the method for checking the patient in at the HCP facility is via the use of technologies comprising readable indicia, including, for example, but not limited to, PINs generated and sent to the patient by BOS, near field communications (NFC), and QR codes. Upon arrival, the patient can scan either an electronic representation of the identifying technology or a paper version of the identifying technology. Upon scanning, the system notifies the HCP's EMR system of the patient's arrival via a security token being passed to BOS to identify the validity of the visiting patient. Accordingly, using the disclosed system, a patient would no longer be required to complete forms regarding changes in their medical record, and the patient would no longer be required to provide medical information from memory, arrive at the HCP with their medications in hand, agree to privacy documentation, nor would she/he need to confirm their insurance information. In addition, the HCP front and back office staff would not be required to manually update patient information, an error-prone process;

gather signatures on privacy disclosures; nor confirm insurance information manually. The HCP is freed to spend more time with their patient, and the patient spends more time with their HCP and less time with paperwork.

In a further embodiment, the system provides a method of paying a patient's co-payment (where appropriate) or paying for a patient's visit directly from the PEMR software using payment methods including Apple pay, Google Wallet, Samsung Pay, PayPal, VISA, MasterCard, American Express, Diners Club, and HSA accounts, amongst other services. The patient will be asked to agree to the payment and select the payment method. Additionally, insurance companies (payors) are able to incorporate the benefits of U. and BOS in their products and services, to drive down costs associated with medical care, errors, and redundant testing of patients.

Patient payment history can be tracked. If records indicate issues regarding patient co-pay, for example, a patient having defaulted on such payments previously, other means can be attempted. Such methods include, but are not limited to, a co-signatory for the payment. At times, a secondary insurance or subsidy, be it private or public, might be charged. Regardless, identification of co-pay difficulty is supported, and it is handled in a manner best suited for the patient and the HCP.

Figure 2:
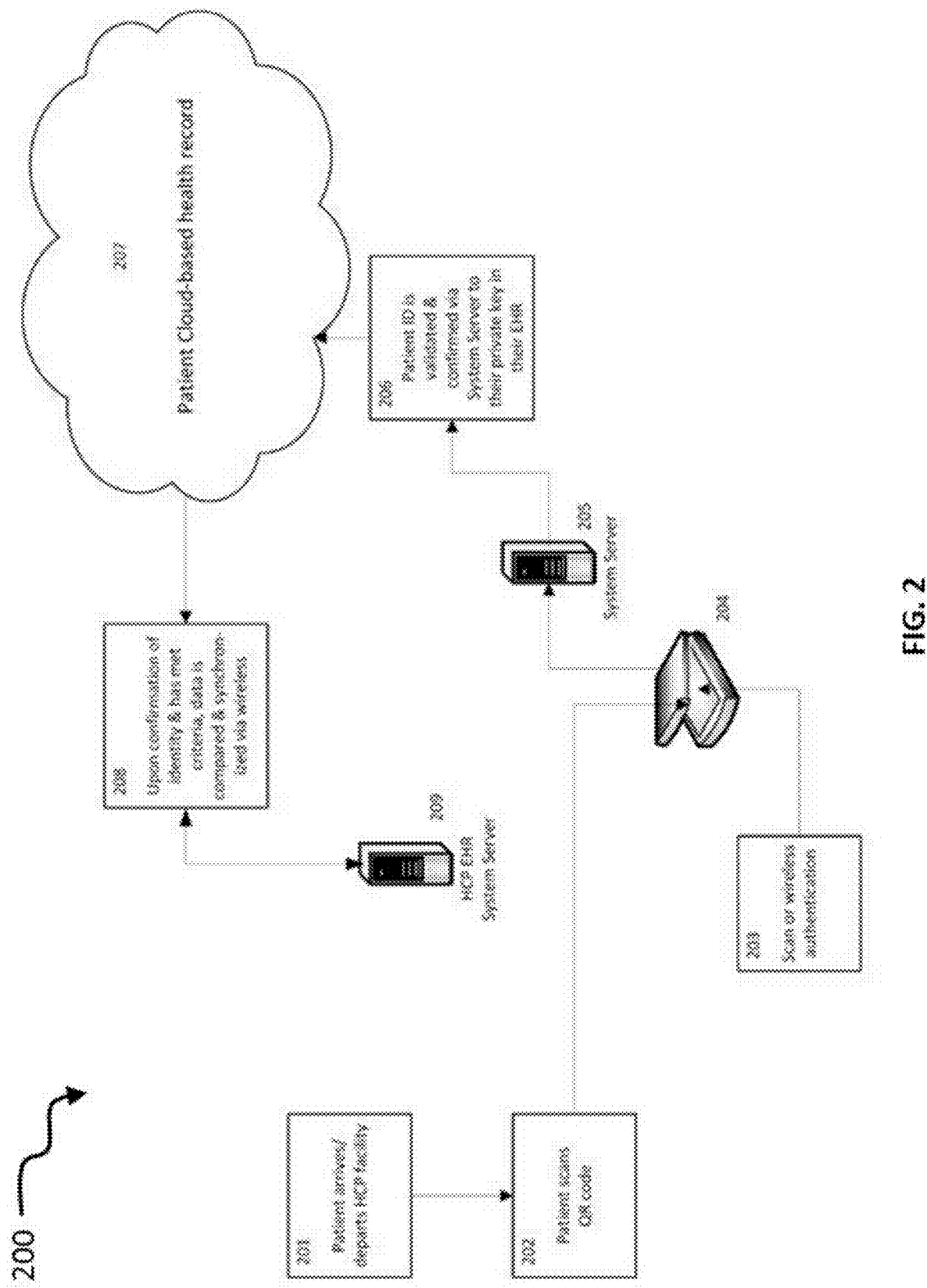
FIG. 2 shows a representative process for authenticating and network-based synchronization, according to one embodiment of the invention.

In various embodiments, the disclosed system utilizes a two-factor authentication model for confirming the identity of the patient upon arrival at the HCP facility. In embodiments of this invention, a mobile device and paper alternative can be used to exclusively identify the patient and securely link the patient to their PEMR. A reason for using the mobile device or alternative methods of authentication is to allow the system to authenticate the patient without moving potentially large volumes of data through cellular networks. Rather, once authenticated, the data are moved between the patient's cloud-based PEMR and the HCP office's EMR system. At no time does the medical record data pass through the mobile device, the cellular network, the patient's home network or public networks (in the case of people using browsers), or BOS. Additionally, in reverse order, changes in the HCP's EHR are synchronized through the system server, through the wireless network, and to the PEMR (FIG. 2). In various embodiments, data can be passed back and forth between the HCP's EMR system and the cloud-based PEMR.

The above-disclosed approach touts multiple advantages. First, at no time are the patient data transmitted over a cellular network. Thus, cellular tapping does not constitute medical data loss. Second, encryption services deployed between the patient's cloud-based PEMR and the HCP's EMR server provide further data security.

In various embodiments, alerts generated by mathematical models functioning within the PEMR cloud infrastructure will notify the patient in real time in the event that their health is placed at risk. By way of example, should the patient be prescribed a medication that has known side effects with the medications currently prescribed to that patient, the patient will be alerted to avoid potentially life-threatening, congenital, or disabling anomalies and death. The same alerts can, at the user's option, be transmitted to one or all of their HCPs or other designated individuals or institutions. In a further embodiment, changes in the patient's record that are of a medical nature will be highlighted for the HCP on a BOS interface, providing them with a summary of changes that can be printed for the provider seeing the patient or viewed in the BOS portal prior to seeing the patient.

In various embodiments, alerts generated by mathematical models functioning within the PEMR cloud infrastructure will notify the patient in real time of predictive health concerns, predictive health recommendations, and predictive long-term implications of treatments or lack of treatment. By way of example, a patient whose key vital statistics are trending toward a condition that could develop should the trend continue (for example, rising A1C levels in the blood can be a predictor of Type-II diabetes) will be notified of the condition and possible outcomes from the condition.

In one embodiment, as regards a patient's scheduled appointment with the HCP, the HCP is able to notify the patient of delays occurring at the HCP facility, allowing the patient to delay arrival or reschedule the appointment dynamically. This embodiment provides the patient with an alert that allows them the flexibility to better organize their daily schedule, rather than sit at the HCP facility for extended periods of time. The HCP facility is able to better manage the patient flow through the facility and provide a higher level of patient satisfaction.

Similarly, the patient's smart device can automatically notify the HCP of a potential delay in arrival. For illustration, consider a patient on route where their smart device can, in real time, determine the scheduled arrival time. Should a delay be expected, the HCP facility is notified of this condition and the HCP facility schedule is modified, minimizing potential HCP facility idle time.

In another embodiment of this invention, patient/HCP interaction is supported via either augmented reality or completely virtual reality. All interactions are logged and encrypted. More so, these interactions can be relayed and augmented or corrected, notifying both parties. Cross-language translation of the interactions and for the individual parties can likewise be supported; thus, the patient is provided with a better understanding of the information provided, enabling them to make a more informed decision.

It is likewise within the scope of this invention to provide mechanisms to further explain or supplement all communication that transpires throughout the patient and HCP interaction. For example, supplementary material in all forms (paper, electronic documents and links, video, etc.) related to the information discussed can be routed to the patient (possibly subject to HCP approval), and the sending of this information is logged in the patient record. Determination of relevant material can be performed using any of the many known-in-the-art information search and relevancy approaches. Thus, patients potentially obtain automatically additional information related to their condition.

In yet a further embodiment, the current and future health care reimbursement structures, in which HCPs are paid in part by the level of patient satisfaction, of the disclosed system processes promote patient satisfaction with their HCP, thereby increasing the HCP's reimbursement.

In yet another further embodiment, the provision of consolidated medical data helps ensure that HCPs do not prescribe treatments that might be detrimental to the patient being treated for other more serious conditions. By way of example, a physician prescribing powerful antibiotics to a patient with an infection, unaware of the fact that the patient suffers from acute kidney disease, would unknowingly place the patient at severe risk of kidney failure, permanent kidney damage, or even death. That same doctor, given a complete medical record, is empowered to consider alternative treatments to avoid further damaging complications for their patient. This insight will promote patient safety and mitigate risks for the physician from a medical and legal perspective.

It is within the scope of this invention to automatically detect contradictions in prescribed treatments. That is, using software systems, in real time, potential restrictions in the form of, for a non-limiting example, alerts, can be issued whenever a drug, device, or treatment is prescribed that contradicts, in the form of an adverse effect or reaction, a patient's previously diagnosed condition or prescribed medication and/or device. Additionally, a global health-care "Recall List" can be compared in real time to ensure that only currently approved treatments are prescribed.

Potential additions to the recall list can be suggested by monitoring patient records for adverse effects. Should an increase of adverse effects pertaining to a particular drug, device, or treatment approach be noted, further investigation of these items is warranted, and the appropriate authorities are notified.

It is likewise an embodiment of the disclosed system that by having access to the full medical record, lifestyle record, and passive data about the patient, the HCP is able to better promote health and well-being rather than merely react to conditions that the patient may develop without proper holistic health advice.

FIG. 1 depicts a representative PEMR server 101, according to one embodiment of this invention, including a system that holds comprehensive health records and passive health data collection capabilities via various sensors commonly termed Internet of Things (IoT), which include, but are not limited to, wireless blood pressure cuffs, scales, EKGs, and a wide range of wearable sensors for each subscribing patient. Additionally, PEMR server 101 maintains medication databases, diagnosis databases, laboratory test databases, and other mechanisms for storing information pertinent to the subscribing patient's health, wellbeing, lifestyle, and medical insurance. The PEMR server 101 can include mathematical models for reactive and predictive analytics. In a further embodiment, the PEMR server 101 comprises configuration databases, security databases, and other databases for use with the functionality within PEMR server 101. The PEMR server 101 can further include a data synchronization component that allows PEMR server 101 to communicate with third-party databases and applications to synchronize data between 101 and, as depicted in FIG. 1, databases and applications such as HCP databases 102, passive data collection devices 103, laboratory instruments 104, pharmacy databases 105, emergency medical facility databases 106, hospital databases and applications 107, other data applications 108, and manually inputted data sources 109. The PEMR server 101 can also include the components for remote authentication for authorizing data transfers between PEMR server 101 and HCP databases 102, passive data collection devices 103, laboratory instruments 104, pharmacy databases 105, emergency medical facility databases 106, hospital databases and applications 107, other data applications 108, and manually inputted data sources 109.

FIG. 2 depicts representative authentication and data replication components and steps of a system according to one embodiment of this invention. Step 201 depicts the patient's arrival and/or departure from the health-care facility. The system requires confirmation that the patient has physically, or in the case of a virtual encounter—virtually, arrived at the facility or has physically (or virtually) left the facility. Steps 202 and 203 depict the patient signing in to the HCP system via the provided QR code, NFC token, or other mechanism developed to authenticate the patient, including a PIN or manually entered code generated by BOS. Step 204 depicts the authentication hardware used to authenticate the patient. Step 205 depicts the system server and software that is used to authenticate and authorize the transfer and replication of data depicted in step 208. Additionally, step 205 comprises scheduling information, including anticipated patient visitation, patient no-shows, and patient visitation or appointment change information. Step 207 shows the PEMR server 101. Step 209 depicts the HCP's EMR system synchronizing with the PEMR server 101. Steps 206 and 208 validate identity and instill security in the data transfer components within the described invention.

Figure 3:
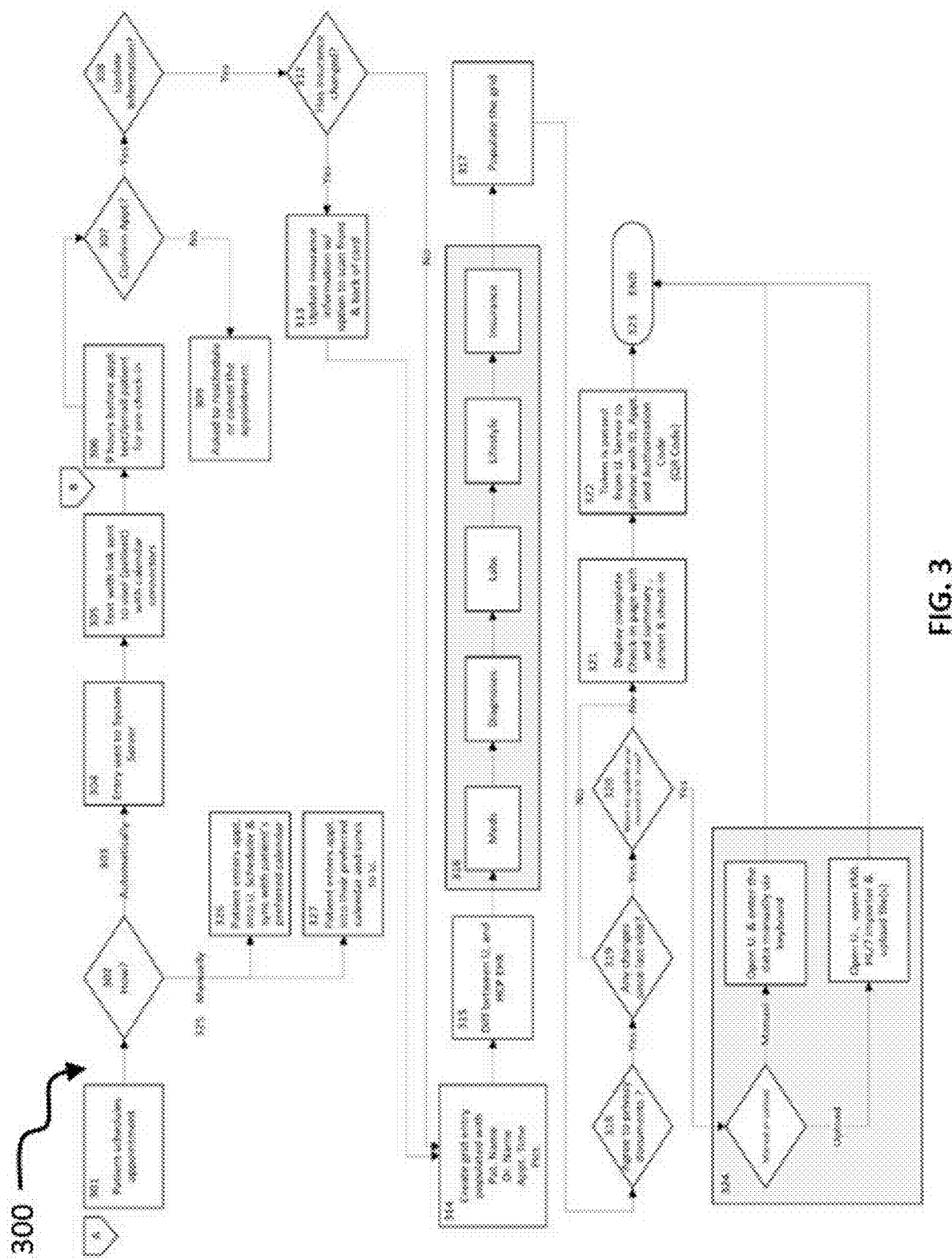
FIG. 3 shows a representative process for consolidating data between a patient's health record and the HCP they are visiting's electronic medical record (EMR) prior to and upon arrival, according to one embodiment of the invention.

FIG. 3 depicts a flow chart 300, according to one embodiment of this invention, in which a patient schedules an appointment 301 with the HCP external to the system described in FIG. 1, 100, and the appointment is synchronized to the PEMR described in FIG. 2, 200, for that specific patient. 300 depicts two modalities (but is not limited to these modalities), the first being an automatic replication and the second being a manual capture of the appointment.

As shown in FIG. 3, flow chart 300 describes the automated method 303 for scheduling the appointment. 304 depicts the transmission of information from the HCP's EMR's scheduler 209 to the system server 205. 305 depicts the mechanism whereby a text message is sent via the SMS protocol and/or an email is sent via standard mail protocols to the patient, which contains a link that facilitates the download of a file allowing the patient to add the appointment to a preferred calendar, including Microsoft Outlook, Gmail, iCal, and any calendar application that supports the .ics shared calendar standard or other current or future calendar standards, thereby allowing the patient to consolidate their medical appointments into their daily schedules. 306 denotes the dispatch of a text via SMS protocol and/or email sent via standard email protocols to the patient, which contains a link that facilitates a pre-check-in process before the scheduled appointment, e.g., at 1, 2, 3, 4, 5, 6, 7, 8, 9, 12, 16, or 24 hours prior to the scheduled appointment. The patient follows the link and is asked to confirm they will be present at their appointment (307); they can be asked if they want to update their health information (308), and they can be asked if their insurance information has changed (312).

In the event that a patient's insurance has changed, they can be prompted to update the information and can be provided the option of scanning or taking a picture of both the front and back of their insurance card to attach to their PEMR (313). In the event that the patient is not able to keep their scheduled appointment, they can be prompted to either reschedule or cancel the appointment (309). In this embodiment, the system may transmit, via BOS, an electronic notification to the HCP's EMR notifying them of the change or cancellation. Scheduling conflicts can be provided via online calendar views provided by the HCP'S EMR.

In some embodiments, upon confirming the appointment, agreeing to the data replication, and acknowledging or correcting insurance information, a grid can be created (314) on the server depicted in FIG. 2, 205, the BUMP Office Server (BOS). The grid may display a comparison of the PEMR record and the HCP's EMR record in the form of the differences between the two categorized (316) by and including, but not limited to, medications, diagnoses, laboratory tests, lifestyle changes, and insurance, as examples. 317 denotes the differences being populated within the grid sorted by appointment time and attending physician, followed by patient name and date of birth. Further to the check-in process, 318 depicts the patient's consent to share their personal and medical information with designated parties and prompts the patient for any changes, medical or non-medical, in their PEMR that might have been omitted for reasons such as delayed laboratory results, new over-the-counter (OTC) product use, new herbal or nutraceutical use, and any other information relevant to the patient's health that might not have been synchronized from their HCP in the past (319).

The patient may select whether or not to update such information as depicted in 319 by declining in 320, or the patient shall be redirected to a mobile platform application to complete this data entry. Finally, the patient is able to complete their pre-check-in process by reviewing a summary of what they have agreed to and selecting the check-in button (321). Upon selecting check-in, a security mechanism (for example, a token) will be passed to the server depicted in FIG. 1, 100. The encoded information shall be sent to the mobile platform application, e.g., an application running on a smart device, including, but not limited to, a smartphone, a tablet, and other such mobile devices. The pre-check-in process then ends (323).

If a patient does not use mobile platforms or technologies, the system can provide a mechanism for completing the pre-check-in via a web browser on a desktop or laptop platform. The process shall be completed as shown in FIG. 3; the automated method for scheduling the appointment. 304 depicts the transmission of information from the HCP's EMR's scheduler 209 to the system server 205. 305 depicts the mechanism whereby a text message is sent via the SMS protocol and/or an email is sent via standard mail protocols to the patient, which contains a link that facilitates the download of a file allowing the patient to add the appointment to their preferred calendar, including Microsoft Outlook, Gmail, and iCal, and any calendar application that supports the .ics shared calendar standard or other current or future calendar standards, thereby allowing the patient to consolidate their medical appointments into their daily schedule. 306 denotes the dispatch of a text via SMS protocol and/or email sent via standard email protocols to the patient, which contains a link that facilitates a pre-check-in process before the scheduled appointment.

The patient can follow the link and is asked to confirm they will be present at their appointment (307); they are asked if they want to update their health information (308), and they are asked if their insurance information has changed (312). In the event that a patient's insurance has changed, they can be prompted to update the information and provided the option of scanning both the front and back of their insurance card to attach to their PEMR (313). In the event that the patient is not able to keep their scheduled appointment, they are prompted to either reschedule or cancel the appointment (309). In this embodiment, the system shall transmit an electronic notification to the HCP's EMR notifying a patient of the change or cancellation. Scheduling conflicts can be provided via online calendar views provided by the HCP's EMR. In a further embodiment, upon confirming the appointment, agreeing to the data replication, and acknowledging or correcting of insurance information, a grid is created (314) on the server depicted in FIG. 2, 205, system server.

The grid can display a comparison of the PEMR record and the HCP's EMR record in the form of the differences between the two categorized (316) by and including, but not limited to, medications, diagnoses, laboratory tests, lifestyle changes, and insurance, as examples. 317 denotes the differences being populated within the grid sorted by appointment time and attending physician, followed by patient name and date of birth. Further to the check-in process, 318 depicts the patient's consent to share their personal and medical information with designated parties and may prompt the patient for any changes, medical or non-medical, in their PEMR that might have been omitted for reasons such as delayed laboratory results, new OTC product use, new herbal or nutraceutical use, and any other information relevant to the patient's health that might not have been synchronized from the HCP in the past (319). The patient may select whether or not to update such information as depicted in 319 by declining in 320, or the patient shall be redirected to their mobile platform application to complete this data entry. Finally, the patient is able to complete their pre-check-in process by reviewing a summary of what they have agreed to and selecting the check-in button (321). Upon selecting check-in, they will be prompted to either send the security QR code, RFID, or PIN to a device or print the QR code, RFID, or PIN to paper. The pre-check-in process then ends (323).

In a further embodiment, the patient is provided a facility for manually updating information about themselves, their medical conditions, medications, OTC and nutraceutical use, and other information via one of two modalities (324). The first modality is manual, in which the user or the patient captures data directly into their PEMR application. The second modality is via the upload of information provided to the patient from the HCP or other sources in XML format compliant with the Health Layer 7 (HL7), which reduces the burden on the patient by uploading information that has changed in their record. Before committing the uploaded data to the database, the PEMR system shall confirm what information is being uploaded and if this information has been superseded by newer information. The patient, at their option, can have three options: the first is to accept the upload and commit it to the database, the second is to decline the upload entirely, and the third is to store the data in a manner in which the newer data remains in focus.

Figure 4:
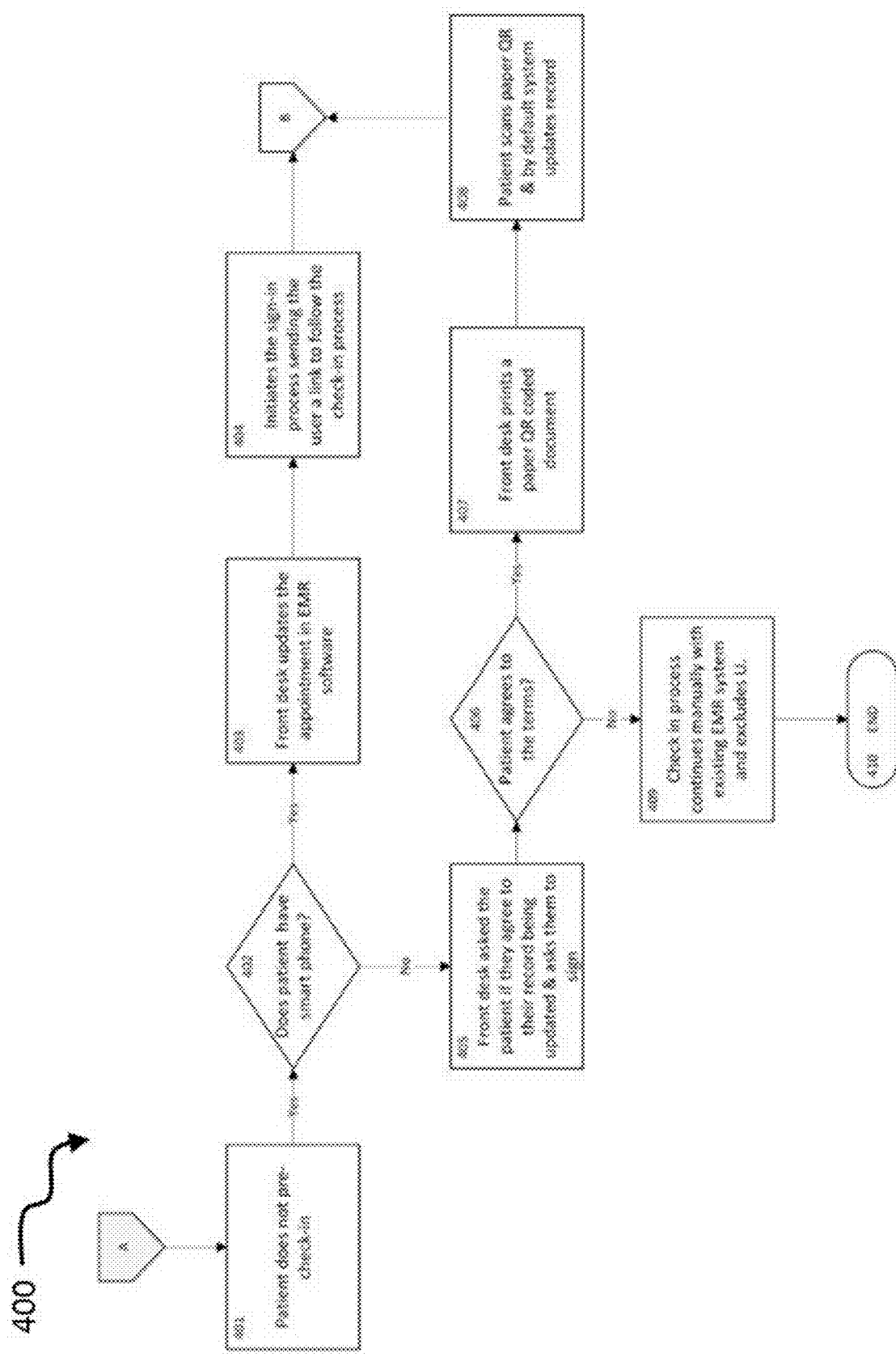
FIG. 4 shows a representative process for an alternative method of synchronizing information or data between a patient's health record and the HCP they are visiting's health record upon arrival, according to one embodiment of the invention.

FIG. 4 depicts a process 400, according to one embodiment, in which the patient is able to use the system despite not using the pre-check-in process depicted in FIG. 4 (401) for reasons that might include ignoring the reminder or a change in their mobile device number or email address on record. In a further embodiment, the system provides two modalities for determining the optimum way of checking the patient in. 402 determines these modalities by inquiring if the patient has a smartphone in their possession. In the first modality, the patient has a smartphone in their possession, the HCP updates or reverifies the patient contact information in the EMR (403), and the HCP scheduling staff sends a confirmation via the HCP's EMR scheduling system (404), which, in turn, resends the text message or email referenced in FIG. 3, 306. The confirmation sends a link, which the patient uses to follow the process 300 depicted in FIG. 3. In the event the patient does not have a smartphone in their possession, the front desk will revert to a manual confirmation of the patient's agreement to share personal medical information and to their medical record being automatically updated, both of which the patient will be required to acknowledge by signing the appropriate form (405). If the patient agrees to these terms (406), the front desk prints out a paper pass encoded with the security information to provide a one-time sign-in access to that patient (407), and the patient checks in (408) by scanning the encoded document, and their record updates based on all changes in both the PEMR and the HCP's EMR systems. In the event the patient declines, the check-in process will continue manually, requiring the patient to complete their medical forms, which will be manually entered into the HCP's EMR system (409). After the completion of either 408 or 409, this process shall be deemed complete.

Figure 5:
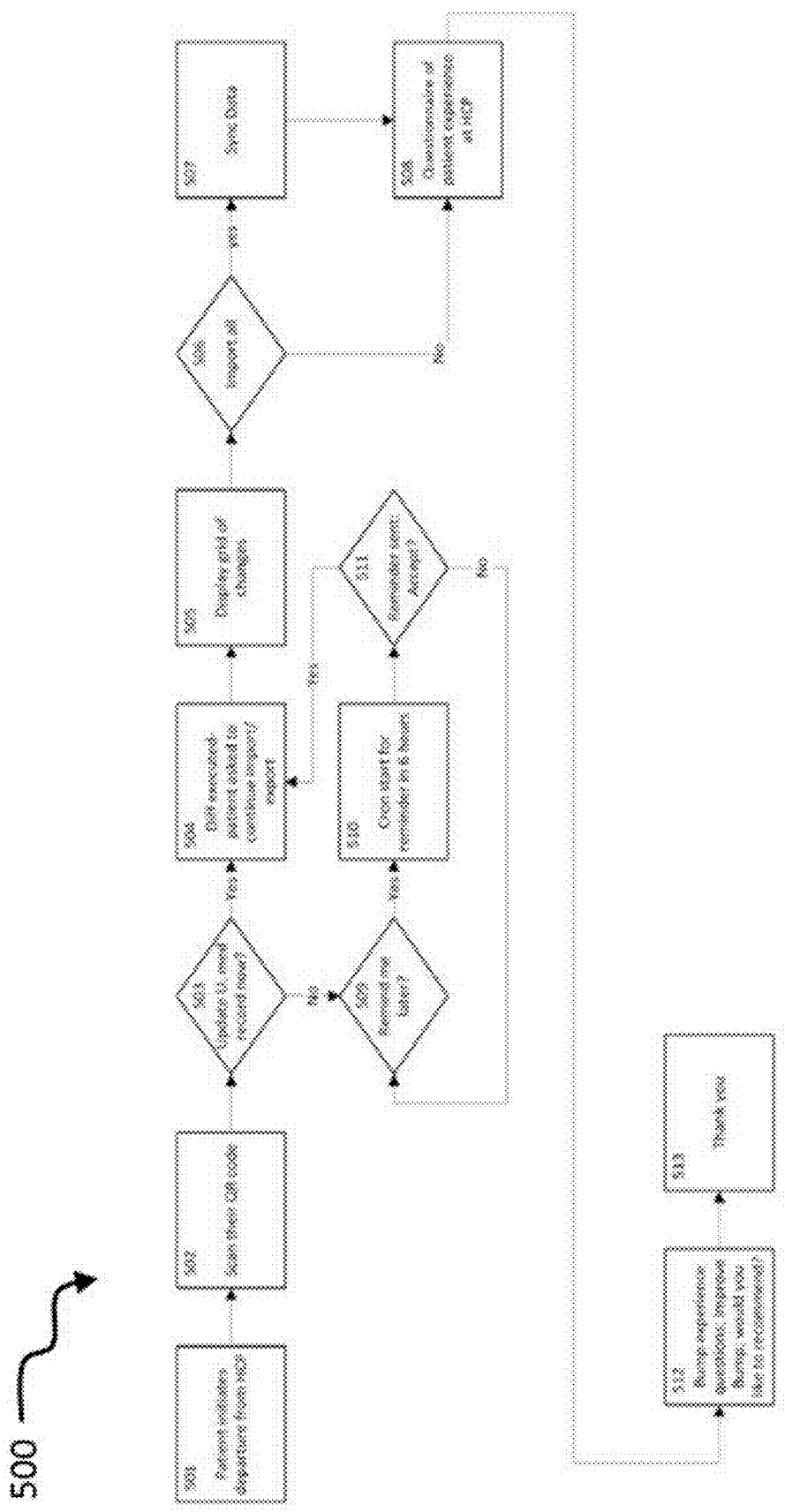
FIG. 5 shows a representative patient departure from the HCP's facility and the method for synchronizing information or data between the HCP's patient's EMR and the patient's EMR, according to one embodiment of the invention.

FIG. 5 which depicts a process 500, according to one embodiment, whereby the patient completes their visitation and checks out of the HCP facility (501). The patient, upon arrival at the check-out desk, scans their encrypted code via either a smartphone or printed encoded QR code, RFID, or PIN (502), either provided by the HCP as depicted in FIG. 4, 407, or printed by the patient in lieu of sending the code to their smartphone. The patient is prompted to allow the new information generated during this visitation to be synchronized with their PEMR (503). The system provides two modalities, the first being receiving the patient's agreement for the replication of data (504) and the second being the option to remind the patient to synchronize the information at a later date (509). In a further embodiment, 504 executes a comparison between the HCP's EMR and the patient's PEMR and displays to the patient a grid of the changes (505). The patient is prompted to import all records (506), and if they agree, the information is synchronized between the HCP's EMR system and the PEMR system (507). In the event the patient elects to be reminded later (509), a timer (Cron) shall be started and set to remind the patient to update their record every regularly (510); in the event the patient accepts the reminder (511), the process beginning with 504 above shall be executed. In the event the reminder is declined (511), the process depicted in 509 shall be repeated. In the embodiment of 506, should the patient decline to import updated information, they can be directed to a questionnaire (508) that captures data about the patient's experience at their HCP. The same can apply after the execution of 507, where once the data replication is complete, a patient can be required to complete the questionnaire in 508. Finally, the system shall survey the patient regarding their experience using the U. application and prompt them to either refer the application to friends or 'like' the system in social media, including, but not limited to, Twitter, Facebook, Instagram, LinkedIn, and others (512). In closing, the patient will be thanked for the information provided in 508 and 512, and the process shall end (513).

Figure 6:
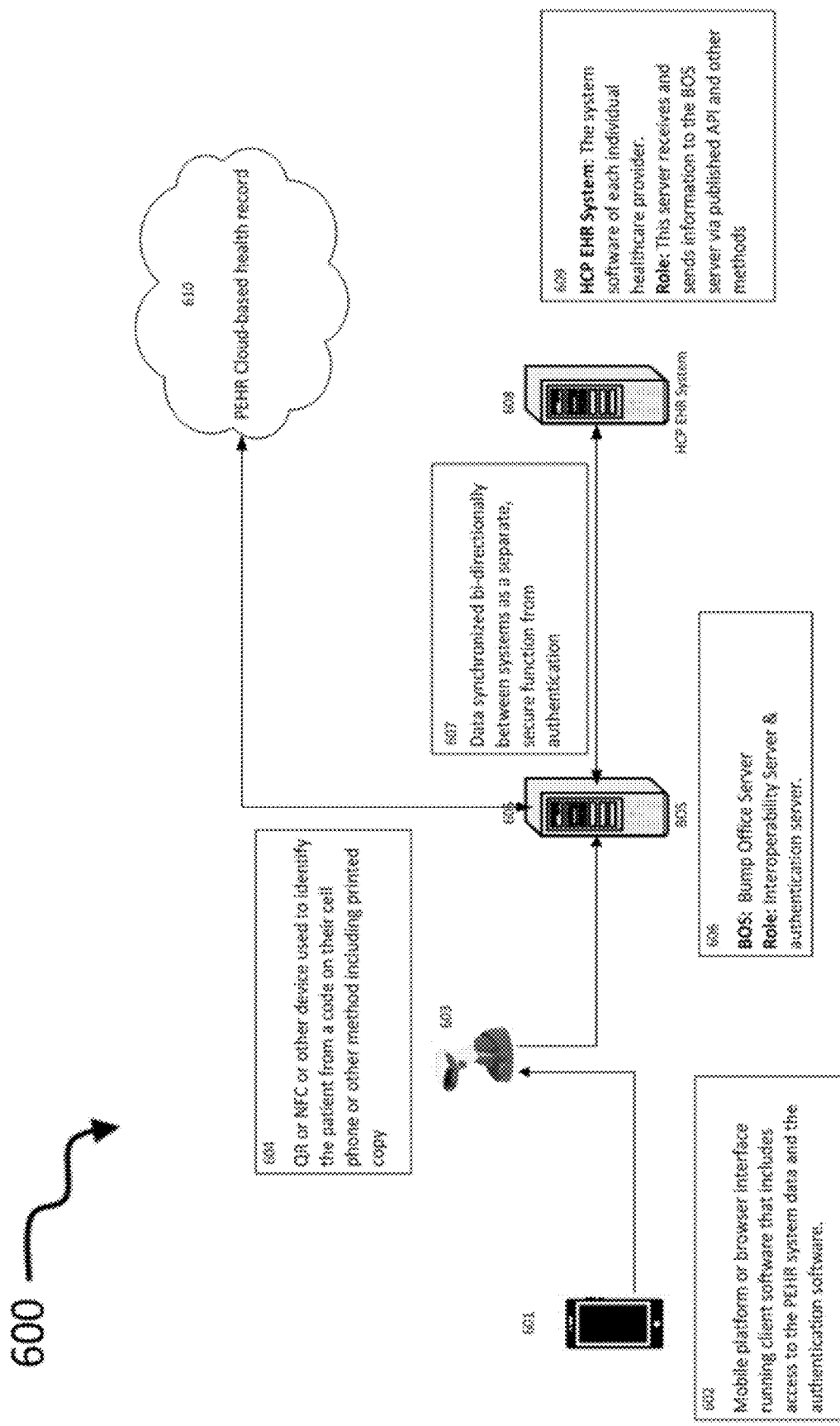
FIG. 6 shows representative components of a system according to one embodiment of the invention, and describes each component's role in the system according to one embodiment of the invention.

FIG. 6 shows a representative system (600), according to one embodiment of the invention. 601 and 602 show the mobile or browser based platform that the patient uses to manage their PEMR via the software installed on the device or accessed via a URL link. 603 and 604 depict the device used for identifying the patient, confirming their arrival for their appointment, and starting the synchronization of the data between BOS and the HCP's EMR server. 605 and 606 depict the BUMP Office Server (BOS), the part of the system that synchronizes a medical record between the patient's PEMR and their HCP's EMR software. 607 describes the process whereby once the patient is identified, verification is received from both patient and HCP to synchronize the data, and once all identification criteria and other criteria are met, the synchronization occurs between the PEMR system and the HCP's EMR system via BOS in an encrypted communication channel with no human involvement in the transmission. Thus, confidentiality and a higher level of security are assured because the transmissions occur randomly and provide no context regarding the nature of the transmission.

Figure 7:
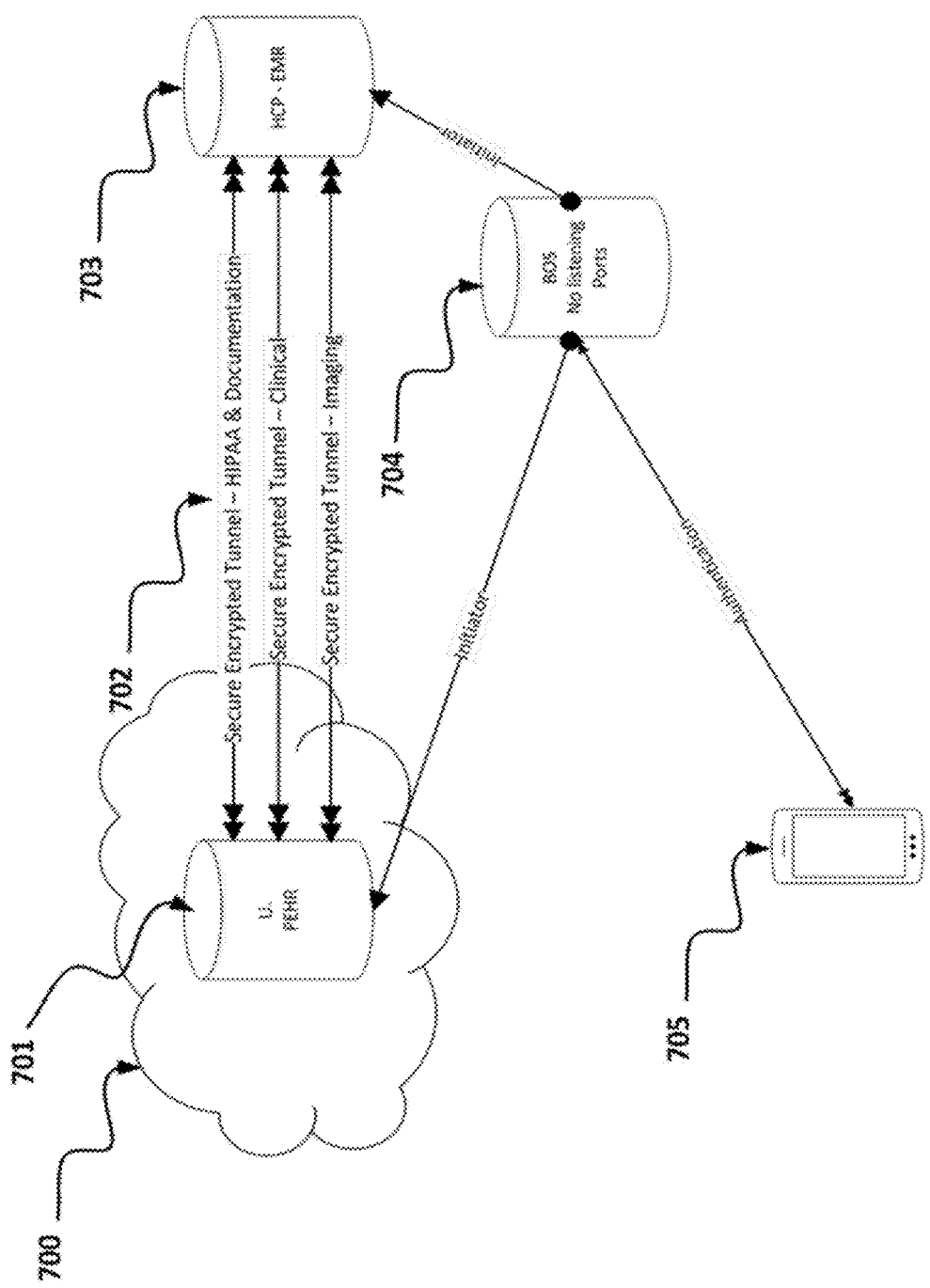
FIG. 7 shows the communication security paradigm deployed in one embodiment of the invention.

In terms of communication security, as shown in FIG. 7, in the communication architecture 700, BOS 704 has no listening ports; it is always the initiator. BOS requests information and collects queued responses from applications. Responses include all confirmations and synchronization requests.

When a record synchronization request is confirmed, BOS spawns a secure channel 702 between the PEMR 701 and the HCP-EMR 703 and then disengages. The synchronizations are decomposed into clinical components without the inclusion of any personal identifiers. No personal information is transmitted as such information is not needed; both the PEMR 701 and the HCP-EMR 703 already know the identity of the patient represented as a mobile authentication device 705. Consequently, static data, such as, but not limited to, date of birth, gender, social security number, ethnicity, etc., are never transmitted.

On some documents signed by the patient (potentially prior to arrival), personal identifiers can be found, and images (x-rays, MRIs, etc.) are potentially likewise decomposed as some of the film can hold some personal identifiers. Regardless, all transmissions are encrypted. For the transmission of either documents or images, the sender (either 701 or 703) initiates a separate secure communication channel as part of the synchronization process. The system encrypts any documents or related media (x-rays, MRIs, etc.) as a separate process from the encrypted clinical data and, in turn, breaks these transmissions into multiple segments, each transmitted using a separate port. Further encryption shall be provided by breaking the transmission into encrypted hashes and reconstituting the hashes once all the segments are received by the receiving system (either 701 or 703). Transmission errors are stored in the application logs and are displayed in the BOS dashboard. Among the benefits of this approach is that security vulnerabilities are mitigated. Regardless of the source of the attack, be it by an HCP office worker or by an external attacker, they do not have access to the transmission; in relation to the clinical data transmission, there is no personal context in the data. For example, the patient's A1C laboratory results might be in the transmission stream, but a number such as 5.2 is meaningless without context.

BOS is configured to have no listening ports open. BOS always initiates all communications and uses a method for polling and messaging to coordinate the synchronization of all information. By restricting all listening functions for BOS, the system ensures that the server cannot be compromised by port scanning and other malfeasant activities attempting to breach security within the system. Further for security, the mobile device is only used to display identification information—such as a pin or a QR code. At no time does any data travel via the phone and the device's connected networks (cellular, TCP/IP, Bluetooth or any other communication mechanism). Finally, BOS never transmits the data; it initiates the communication between the PEMR (701) and the HCP-EMR (703), further hardening the environment from a security perspective.

Continuing with FIGS. 6, 608 and 609 show the HCP's EMR system that is not part of this application and is represented as a required component for the effective implementation of the system. 610 represents the PEMR system, the cloud-based, patient-controlled EMR software.

Figure 8A:
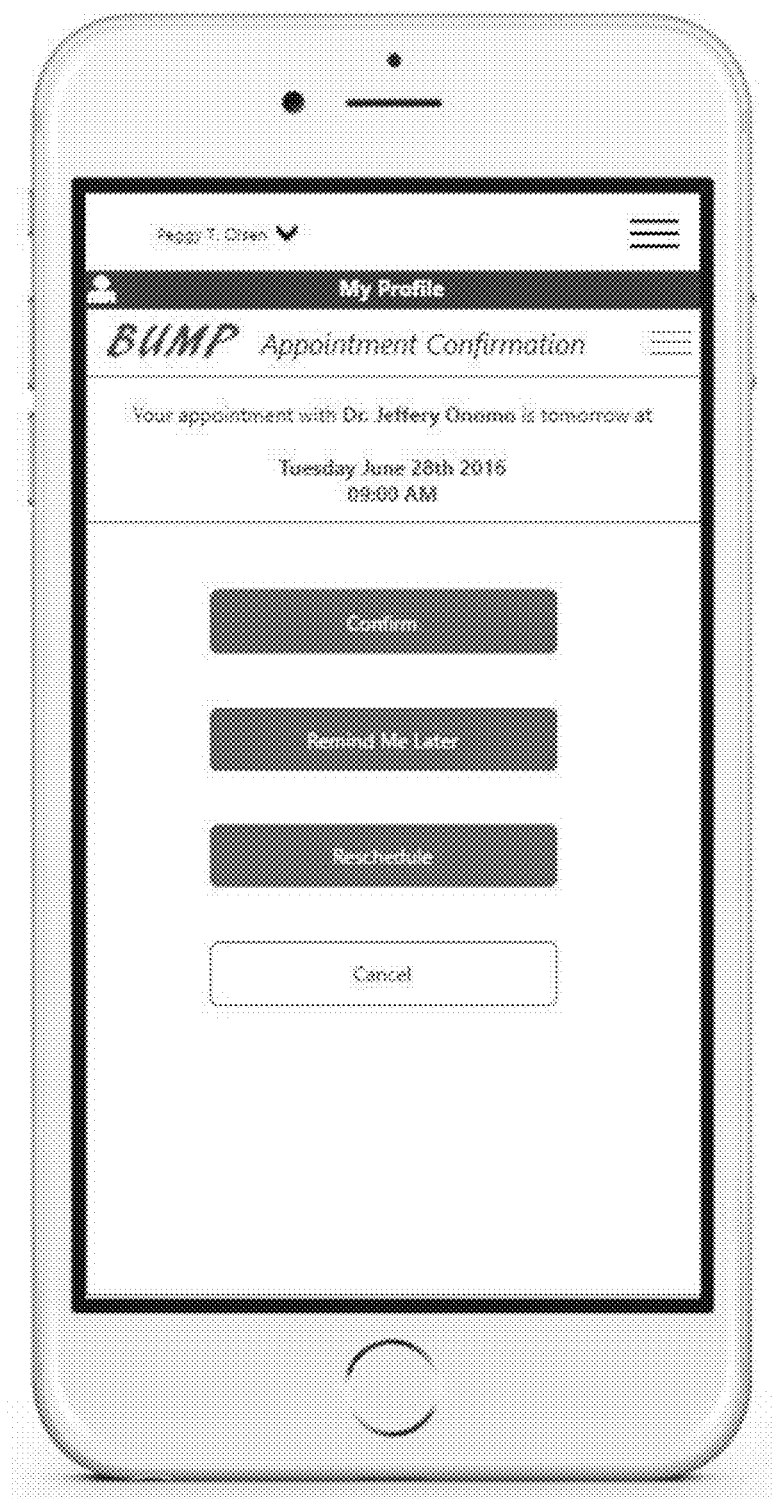
FIGS. 8A-E each shows a mobile device at a corresponding step of a representative implementation, according to embodiments of this invention.
Figure 8B:
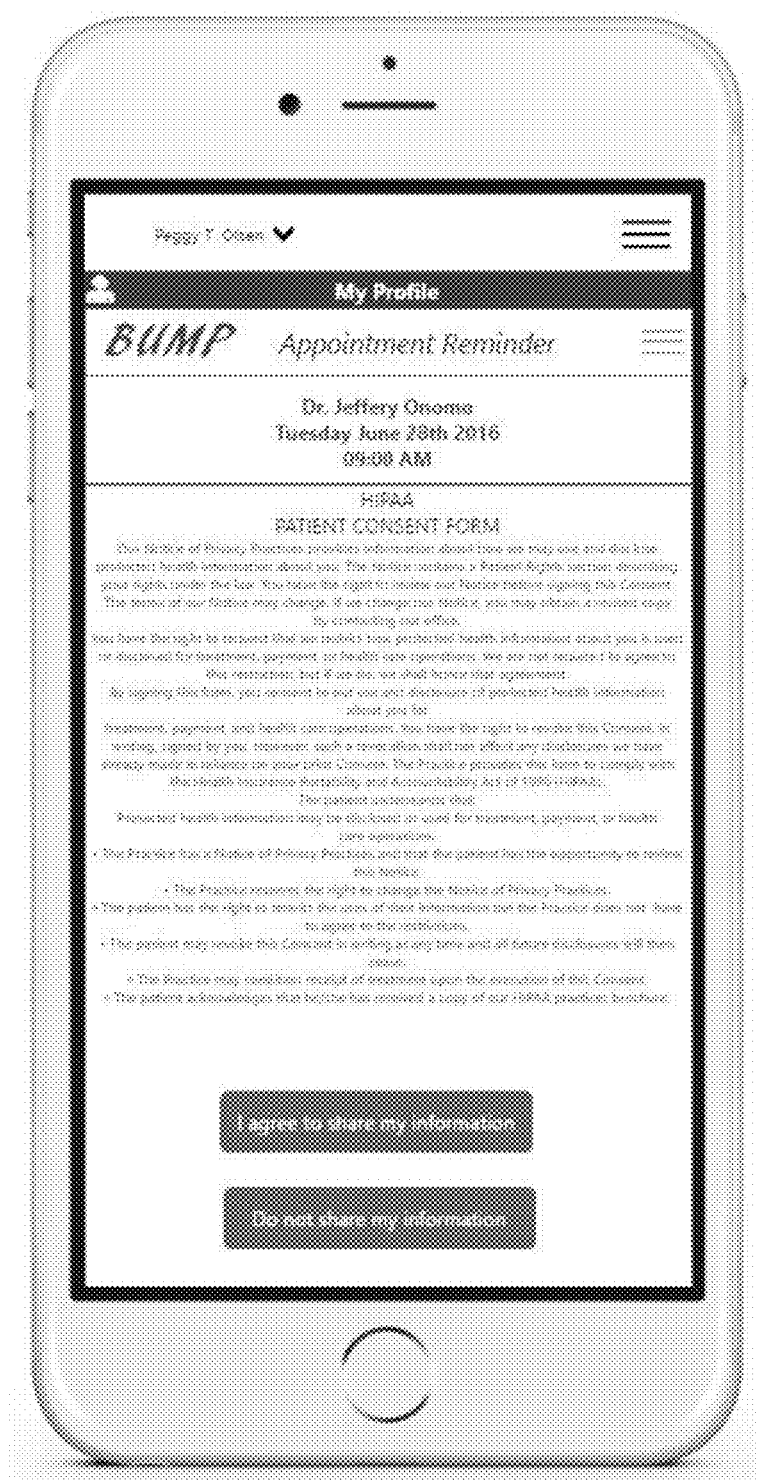
Figure 8C:
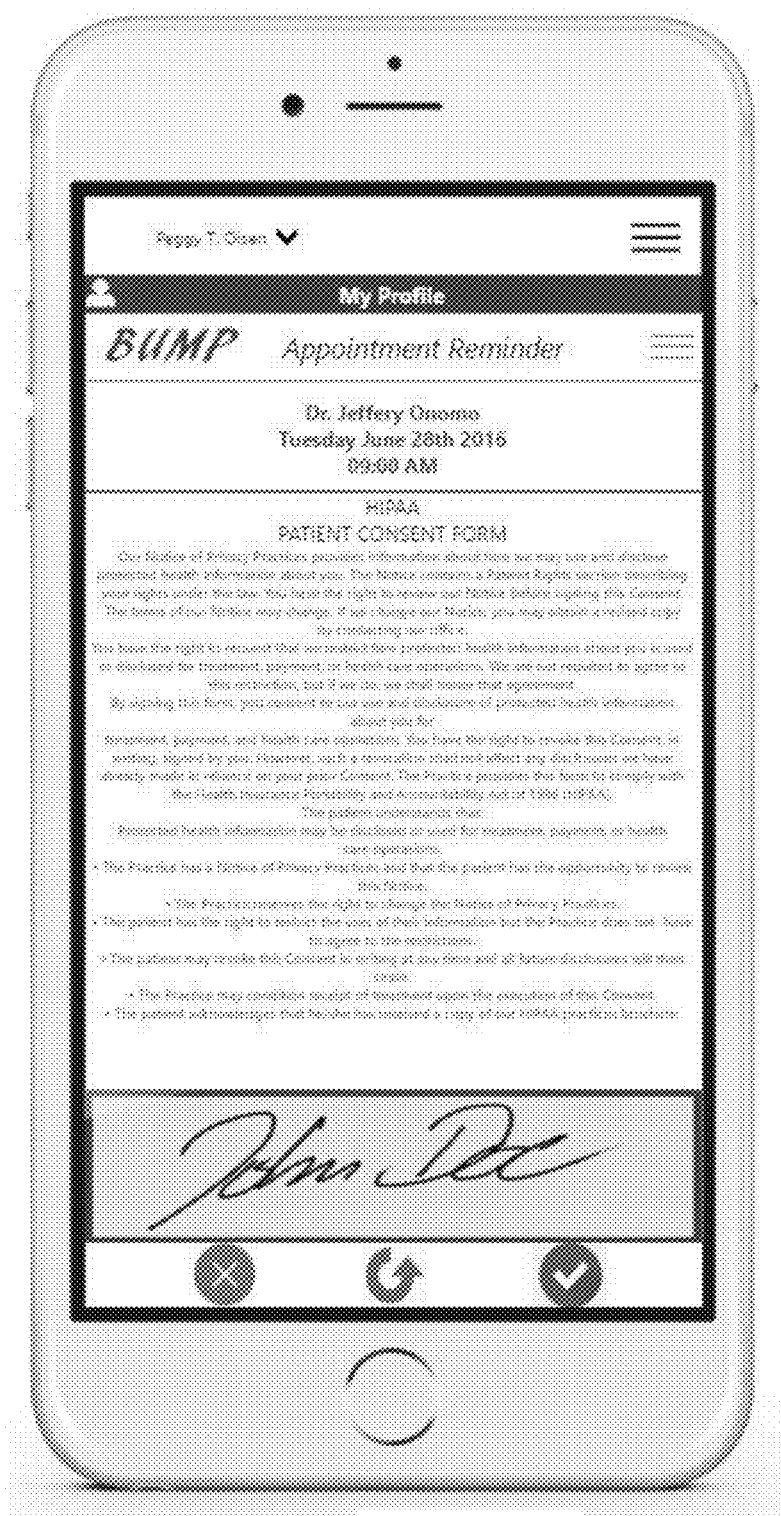
Figure 8D:
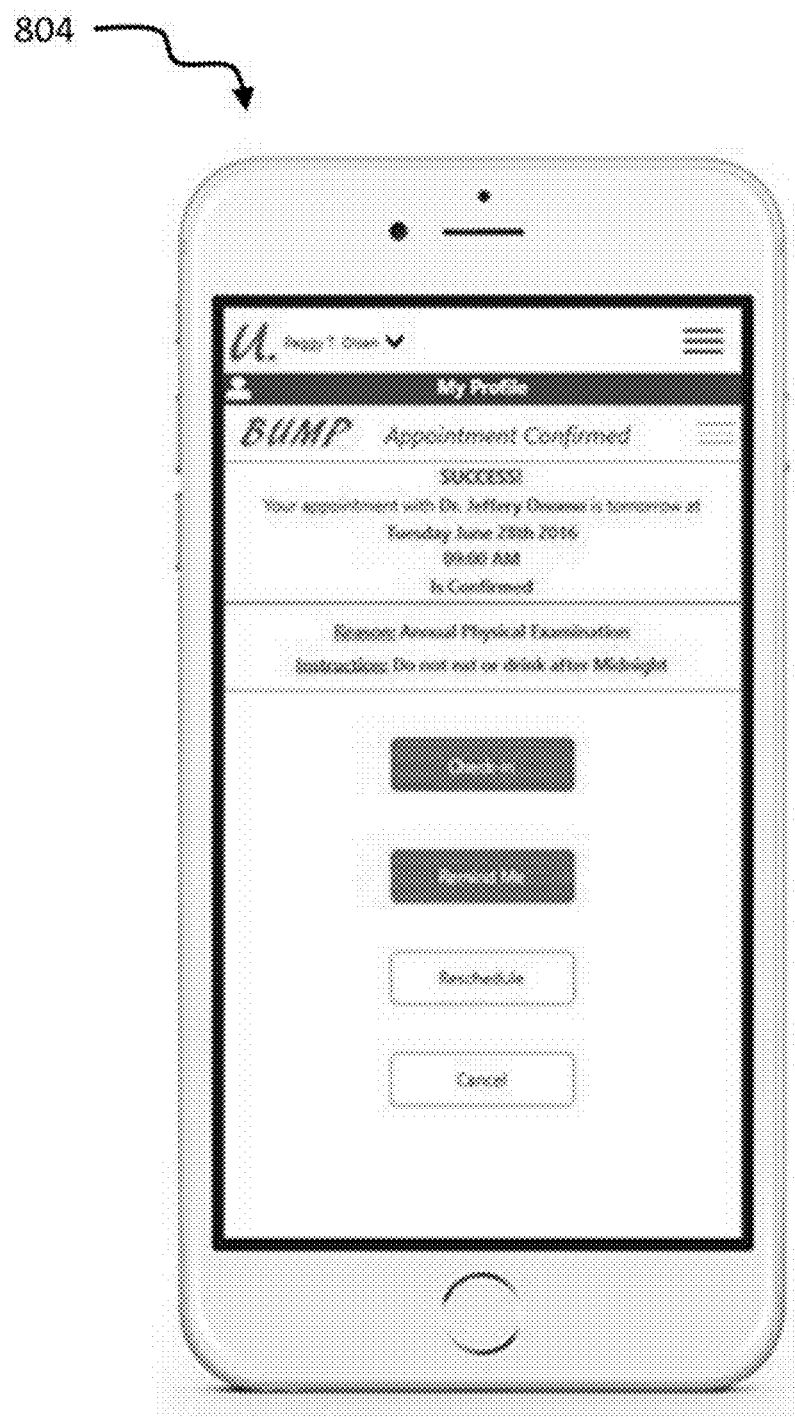
Figure 8E:

FIGS. 8A-F, collectively illustrate a representative implementation of a mobile platform application of one embodiment, referred to in this disclosure as the "U. application." In some embodiments, the U. application can comprise such exemplary software components as an appointment confirmation component 801 (FIG. 8A). The appointment confirmation component comprises a user interface providing a reminder of a forthcoming appointment that a patient has with an HCP, and further provides various options for patient input regarding the appointment with the HCP. In a further embodiment, the U. application can comprise an appointment confirmation component further comprising a patient consent form component 802 (FIG. 8B). The appointment confirmation component further comprising a patient consent form component can enable a patient to provide HIPAA consent, via clicking a displayed choice(s) that a patient can select, to share medical information with the HCP with whom the patient has an appointment. In various embodiments, the patient consent form component can further comprise an electronic digital signature input, 803, from the patient providing consent (FIG. 8C). In some embodiments, the patient consent form component can link from component 802 to component 803 if a patient selects the option of providing consent, thereby requiring not only affirmative input from the patient in component 802, but also an electronic digital signature in component 803. In a further embodiment, the U. application can comprise an appointment confirmation component further comprising a patient check-in component 804 (FIG. 8D). In various embodiments, the U. application can comprise an appointment confirmation component further comprising a readable indicia component 805 (FIG. 8E). In a further embodiment, a patient, upon selecting the option to check in for an appointment in component 804, can be presented with component 805, wherein a suitable readable index is provided for use at the HCP provider office. As shown in FIG. 8E, the readable indicia can be a QR code, RFID, or PIN; however, other readable indicia formats can be used as described herein.

In a further embodiment, the disclosed system and processes can comprise a client system that can provide synchronization with HCPs, including emergency medical providers, such as emergency medical technicians (EMTs) or emergency room (ER) providers such as physicians, nurses, nurse practitioners, and physician assistants. Synchronization to emergency medical providers can further protect the health and safety of a patient using the software. It is anticipated that leveraging such data provided by the disclosed systems and processes can provide significant clinical value in the event that the patient is in a dire medical situation in which the patient is in a critical medical condition and/or in which they may be non-compos mentis. In such situations, lives can be saved or lost depending upon how quickly EMTs, ER personnel, first responders, and the like have a full medical history of the patient to whom they are rendering care. The disclosed systems and processes, via the use of a mobile platform, can provide a mechanism in which, even when the patient's screen is locked (secured) and the application is secured, medical professionals are still able to access the patient's PEMR.

Figure 9A:
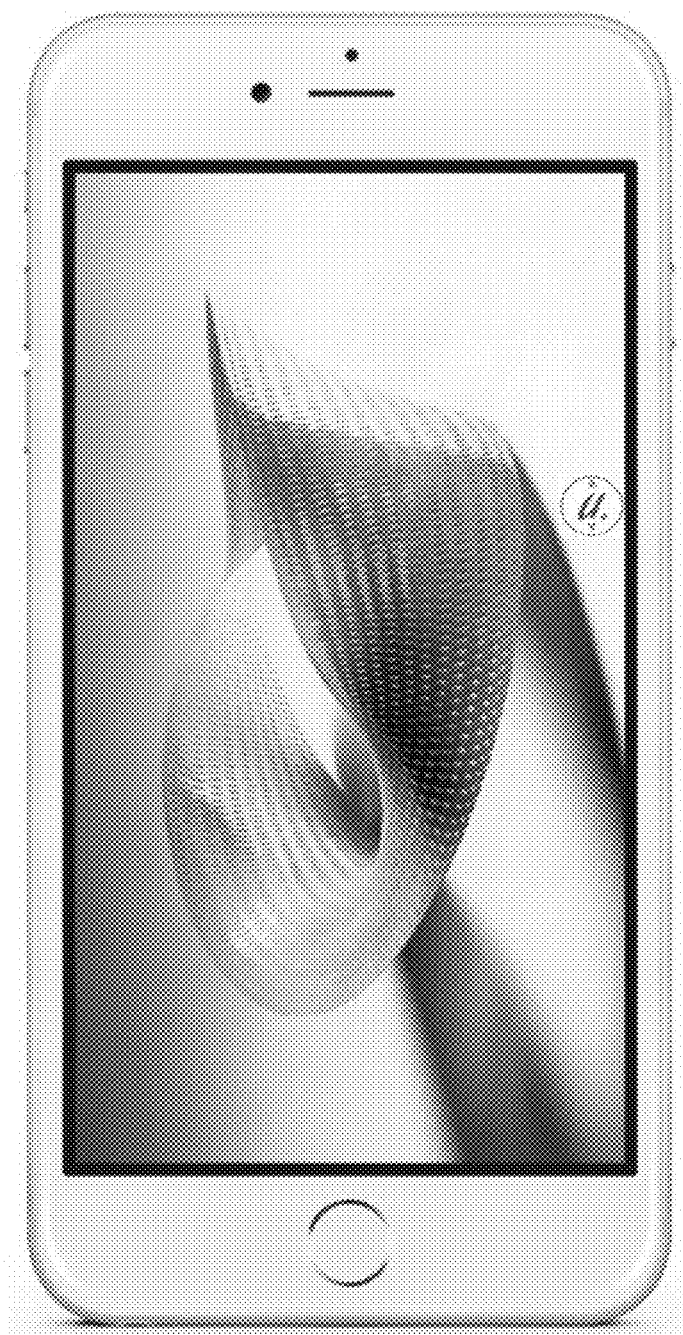
FIGS. 9A-F each shows a mobile device at a corresponding step of a representative implementation, according to embodiments of this invention.
Figure 9B:
Figure 9C:
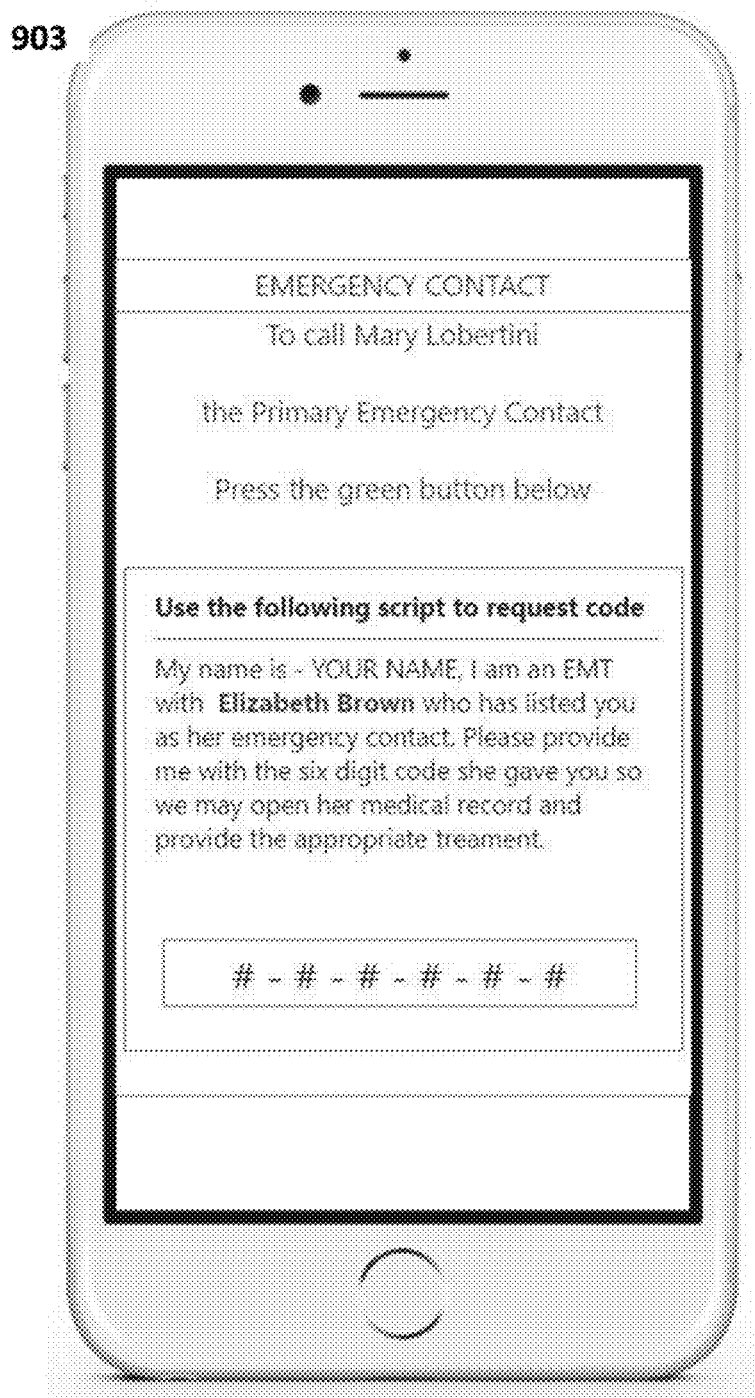
Figure 9D:
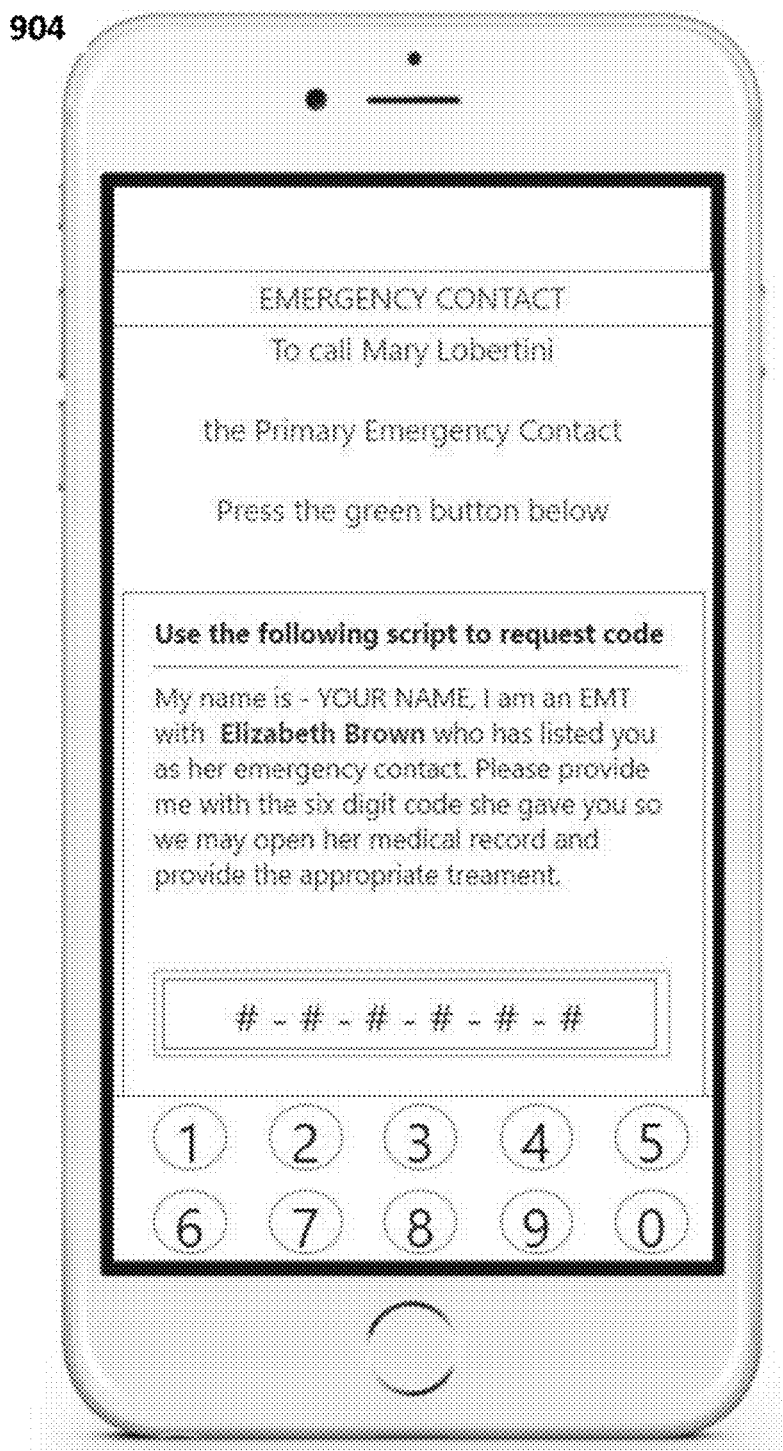
Figure 9E:
Figure 9F:

In various embodiments, emergency personnel can access a PEMR using a patient's mobile platform via a function represented as a floating icon that is persistent on the user interface even when the screen is locked. Swiping the icon FIG. 9A (901) up or down on the screen will result in the system identifying the first of the patient's registered emergency contacts listed in their private record being displayed on the screen with the dial button displayed FIG. 9B (902). The system can dial the emergency contact's default number and each emergency contact's number in order of priority in their record until the call is answered by the contact who can provide the emergency personnel with a 6-digit code FIG. 9C (903) that they enter on the screen FIG. 9D (904) and FIG. 9E (905) to release a medical record in a non-edit mode (view only) FIG. 9F (906). In the event that all the default emergency contact's numbers are exhausted, the next emergency contact is contacted via the same mechanism.

In various embodiments, emergency personnel are able to render safe and effective treatment to the patient. By way of an example, a patient might lose consciousness with all the symptoms of congestive heart failure, and in many cases, the treatment would be effective and lifesaving. However, for the purposes of this example, the patient may be experiencing a severe food allergy that can manifest with the same symptoms as congestive heart failure. In this example, if a patient does not have the proper medication infused within a short period of time, the patient's airways can swell up until the air passages close and result in the death of the patient. A complete medical record could allow emergency personnel to determine that the patient had a food allergy and, as a result, the emergency personnel are able to administer the proper treatment to save this patient's life. In the absence of such knowledge, a patient could perish.

In various embodiments, the disclosed systems and processes can enhance the ability of HCPs and health-care organizations to identify and report patient drug adverse events (AEs) and serious adverse events (SAEs). In some embodiments, the disclosed systems and processes can provide for enhanced patient adherence to the prescribed dosage instructions. In a further embodiment, the disclosed systems and processes can provide an HCP with a tool to configure and upload adherence instructions and schedules to the patient's application, e.g., U. application. For example, an HCP can use a simple interface to identify the medication, route of administration, frequency, dosage, interval between doses, and further instructions for the safe use of the medication. When an HCP transmits the file via the system to the patient, the patient can accept the file, and upon patient acceptance, adherence instructions can be added to their mobile platform application. Once uploaded, the instructions for use of a given medication are coordinated to a prescribed schedule. For example, if the patient is instructed to take 50 mg of a medication twice a day, with six hours between doses, with food, for two weeks, the mobile device platform, comprising the mobile device software, can remind the patient via a mechanism specified by the patient (e.g., SMS/text, email, and/or notification directly on their mobile platform device or other computing platform).

In various embodiments, the disclosed systems and processes can enhance the ability of HCPs and health-care organizations to identify and report patient positive events or outcomes (PEs). While industry, regulatory agencies, and HCPs focus almost exclusively on the negative aspects of drug side effects, no platforms track the efficacy of a medication, therapy, or device in terms of the positive impact of said products. The disclosed invention provides the patient with the ability to report when a product has resolved or is resolving a problem. In other words, when it has worked or is working. This capability is essential when understanding the cohort in which this product was effective; for example, it might be effective in treating Type II diabetes in females in their late 60s of Hispanic descent. In some cases, the product may be effective in an area as yet not approved for this use or configuration.

In a further embodiment, the disclosed systems and processes can provide for tracking adherence to the instructions provided by the HCP. In addition to regular reminders, the patient can be asked to confirm on their mobile device platform or other computing platform whether they have taken the medication. Additionally, a patient is prompted to confirm whether they have followed specific prescribed instructions (i.e., taken with food, on an empty stomach, etc.). If they report that they did not take the medication, the system can prompt the patient for input regarding the reason for non-adherence, including input of the various issue(s) experienced by the patient. Input from the patient regarding the reason for non-adherence can be menu or option-driven presentation of set variables selected by the patient and/or free-form input from the patient providing a description. Free-form input from the patient can be textual or voice input. The mobile device platform application can prompt the user to determine if they stopped taking the medication as a result of some specific event, which may be negative or positive, and accordingly, the information can be used to determine if a drug AE or SAE has occurred. In a further embodiment, in the event a patient can respond that the medication was creating a problem, the mobile device platform software can prompt the patient to report this event immediately to a member of their care team, the manufacturer of the medication, and/or the appropriate drug regulatory authority. Although for some medications, a non-adherence event can be benign, other medications can be associated with serious health implications for the patient if there is non-adherence; e.g., certain medications are associated with extremely harmful or fatal events if use is abruptly ceased.

It is within the scope of this invention that all interaction will be in one or more languages specified by the user.

Thus, the disclosed systems and processes can provide the ability to communicate to the patient, the HCP, and manufacturer information from the patient at the time the event, e.g., AE or SAE, is experienced. Real time, automated, event-based patient reporting to an HCP and/or therapeutic manufacturer is currently unprecedented. This is important because as time passes, patients typically forget specific details about the circumstances of the event that occurred. The sooner they are asked about the event, the more reliable the data the HCP or manufacturer has to work with to determine the cause. With the patient's permission, the HCP and/or manufacturer can have access to the concomitant medications that the patient has been prescribed, over-the-counter (OTC) medications, and any herbal or nutraceutical products they are utilizing. Additionally, the HCP and/or therapeutic manufacturer can have real time information about circumstances around the event, including the following: food consumed (type & quantity), activities, socio-economic conditions, and other information the patient deems worth sharing.

In some embodiments, the disclosed systems and processes can provide previously unprecedented patient data analytics that identify trends. In a further embodiment, the disclosed systems and processes can further comprise software components that can provide automated early warnings, alerts, and recalls. That is, the disclosed systems and processes can comprise a comprehensive communications platform to manage data, analyze the data to identify potential patient trends, and disseminate automated warnings, alerts, and recalls.

In one embodiment, the disclosed systems and processes can comprise a data aggregation component that can aggregate reported AEs and SAEs in a system database(s). The data aggregation component can further comprise algorithms and artificial intelligence modules to identify trends. The data aggregation component can further comprise a communications component that can provide an HCP and/or therapeutic manufacturer notification and details on the identified trends. For example, the data aggregation component can comprise aspects to identify a defined cohort within the population of the users of the medication who are having an unexpected and serious adverse event as a result of several contributing factors, including the suspect drug. Thus, an HCP and therapeutic manufacturer can be provided with a mechanism for contacting the patients within the defined cohort quickly with detailed instructions as to how they should proceed.

The aggregated data can be mined to identify a specific population affected by an adverse condition. That is, group demographics of the affected population can be ascertained. For example, the age range, gender, or race of the most susceptible population can be determined. The religious or family background that potentially implies susceptibility to specific genetic conditions can likewise be detected. Similarly, other non-physical characteristics such as hobbies (e.g., sky diving, hence high altitudes or diving, hence ear pressure), occupation (e.g., indicating potential stress), and potentially unhealthy habits (e.g., smoking or excessive drinking) might all suggest the cause of potential problems. Such aggregations, via mining, are potentially useful in explaining an observed increased prevalence of an adverse reaction.

In addition to the aforementioned leverage with respect to the AEs, SAES, and population groupings, the system will leverage the data to determine "micro-epidemiological" trends in which highly localized areas can be identified, where an outbreak of, for example, influenza is occurring. The ability to see early trends affects several areas of the health and health care delivery:

Early detection of micro-regions being affected by disease
Optimizing supply chains to respond to these early signals to ensure the correct therapies (drugs, vaccines, etc.) are shipped to the affected areas using the principles of "Just in Time" (JIT) principles of highly optimized supply chain systems can be leveraged to stem the spread of disease beyond the micro-regions.

To illustrate this, consider the circumstance where an ER in a regional hospital is starting to treat cases of a specific strain of flu not yet identified as a strain that is affecting that area. As information about the care of these patients is aggregated, it will become evident at the hospital and its supporting ecosystem of HCPs that there is an outbreak of flu that was not anticipated by the vaccines administered in the area. This early warning will allow a response by the vaccine providers to ensure they ship the specific vaccine to this micro-region to avoid the spread of this contagion beyond the area in which this "micro-epidemic" is occurring.

The aforementioned identification can occur in a retrospective assessment of an identified adverse condition; however, the database can similarly be used to identify or isolate a specific population ideally suited for a potential drug or device study. By identifying cohorts with specific characteristics of interest, a target population can easily be identified.

It is likewise within the scope of this invention to ascertain the key traits of a population that has stopped taking a prescribed medication. While there are many reasons why a given patient might forgo a prescribed medication, if a determined trait is dominant among patients prematurely stopping the medication but is rare in the general patient population, then investigating that identified trait as a potential negative factor is possible, and an alternate prescription can be prescribed.

The system provides a facility to further drive costs of medical care down by allowing the patient to receive coupons, samples, and/or rebates directly from, for example, manufacturers. This would consist of targeted products and service offers based on the diagnosis & proposed treatment of the patient. The patient would receive this "perk" upon check-out and before, for example, they visited the pharmacy to fill a script. If a statin had been prescribed, the manufacturer could provide a coupon as an incentive to have the script filled, or a competitor could offer a better, less expensive option.

Further, by integrating the pharmacy (for example), the metrics as to the patient's behavior after their office visit can be analyzed, providing several advantages to the HCP who would have the "proof" that the patient did not follow their recommendations in the event the patient experiences some sort of medical consequence that puts the HCP at potential risk in the current environment.

Currently, manufacturers are not privy to the medications that a patient is prescribed. As a result, the product recall process is cumbersome, is inaccurate, and, in some cases, can cause panic in the general population when recalls are announced via the media and tort attorneys. If the recall does not affect all patients, there is confusion about who is actually affected by the recall. The currently available systems use a mechanism called the "Dear Physician Letter" (DPL), which is a physical letter sent out by the manufacturer, via the postal service, to HCPs with instructions as to how to proceed with, for example, a total withdrawal/recall of a product.

There are two major drawbacks to the currently available systems for providing HCPs with information regarding AEs and SAEs. First, it becomes the responsibility of the physician and their office to track down the relevant patients, contact them, and provide them with instructions for cessation of use of the product, reduction of dosage, or other instructions determined by the manufacturer. They may require the patient to visit their premises to explain the circumstances and implications of the recall. Moreover, there is simply no guarantee that the DPL will be received by the relevant HCP. For example, an HCP may have relocated, changed their practice, or are no longer treating the patient (and are, consequently, without a means of contacting their former patient). All the scenarios described above, as well as multiple other scenarios not described herein, present unacceptable risks to the patient in terms of their health, and for the HCP or the manufacturer in terms of legal exposure. Additionally, the presently available cumbersome and unreliable system places undue administrative burden on HCP providers at a time when compensation is down and they are inundated with compliance documentation. Second, it can take weeks, if not months, for an HCP, once informed by the DPL, to make contact with the affected patients and start the required remedial action. Clearly, the currently available system places a patient's health in serious jeopardy, particularly those patients who are unable to be notified at all, as the patient continues to use a product that could be causing short-, medium-, and/or long-term damage to them.

The disclosed systems and processes provide a number of unprecedented benefits compared to the above-described currently available system. For example, HCPs and manufacturers can reach out to patients quickly and efficiently with clear instructions as to the remedial action they must take to mitigate the risk to their health. In addition, therapeutic manufacturers can identify "at risk" cohorts to quickly and efficiently notify those patients in the cohort of the product issue while allowing patients who are not "at risk" to continue to receive the benefits from the product. In the event of a total recall, the mechanisms within disclosed systems and processes can facilitate faster, more precise recalls of the product. In the event of a recall of a tainted batch of a product, the disclosed systems and process can allow a therapeutic manufacturer to conduct precise, targeted recalls. Finally, the disclosed systems and processes can allow a therapeutic manufacturer to interact directly with the consumers of its products.

The disclosed system supports epidemiological studies and, thus, early detection of outbreaks. Typically, outbreaks, e.g., diseases or adverse drug reactions, are identified via human interactions. That is, HCPs or pharmacies identify increases in illness prevalence or medication demands, and then they notify centralized services, such as the CDC, for further action. However, such procedures often involve significant human effort and introduce delays in identification and notification. In contrast, by maintaining up-to-date, large-scale patient records, it is possible to detect such outbreaks in real or near real time using automated means. Additionally, these detections can isolate geographic partitions, population partitions, or combinations thereof. Hence, detection is quicker, more reliable, more accurate, and less resource demanding. As such, the disclosed approach enables the continuous monitoring (via data mining and other trend detection techniques known in the art) of the state of health of the patient population.

Having detected the outbreak in their onset, resource planning is supported. That is, it is within the scope of this invention to forewarn HCPs, hospitals, and other patient care centers of a likely increase in resource demands. Similarly, pharmacies can be given notice to "stock up" on appropriate medications.

It is likewise within the scope of this invention to support an advertising service to both patients and HCPs who participate in the disclosed invention. Subscriptions to advertisers to target, such as, but not limited to physicians, pharmacies, and pharmaceuticals, can be sold. Advertisements to both patients and HCPs informing them of availability and possible discounting of services or supplies can be sent. Coupons can likewise be distributed. Participation in said advertisements and coupons can save time and effort in locating a physician or good, and can reduce cost to both HCPs and patients. Patients and HCPs can "opt in" or "opt out" of said notifications. In addition to potentially assisting both patients and HCPs, those maintaining the disclosed system can collect revenue from advertisers, increasing the profitability of the disclosed approach.

FIGS. 10-14 illustrate a medical data flow according to embodiments of this invention. A first component of the system of this invention resides at a first doctor site 1000, and includes of a link from the local (doctor's) EMR 1002 to the BOS 1004. The BOS 1004 desirably supports a wide range of communication and data exchange protocols and standards as it may need to interface with each of the many diverse EMRs available worldwide, including but not limited to those sold by Cerner Corporation and Epic Systems Corporation. Additionally, the BOS 1004 desirably supports standards other than those related to EMRs including, but not limited to, imaging (e.g., DICOM), HL7 genetics standards, pharmacy standards, laboratory standards, regulatory standards, and dietary and fitness standards.

A second system component, a cloud based database 1010, stores all the PEMRs, in a secure and distributed manner, such as described below. At the center however, and ever present, is the patient (not illustrated). In the invaryant system of this invention, the medical data available to the treating HCP (doctor), at the moment of diagnosis and treatment, are desirably complete and up-to-date. That is, every patient treatment relies on a complete, real-time accurate PEMR. This contrasts, however, with any potentially corresponding, locally resident EMR entries at any non-currently treating HCPs that are potentially dated, hence incomplete. However, if and when the data are used for treatment, namely, the local site becomes an immediate treatment center, these local EMRs are made complete (updated) prior to their use. Note that the PEMRs stored at database 1010 are always the most accurate medical record for that patient with the last HCP that patient visited having the most recently updated EMR of that patient's treating physicians. When the patient visits another provider or a new provider, that provider's EMR becomes the most current record.

Figure 10:
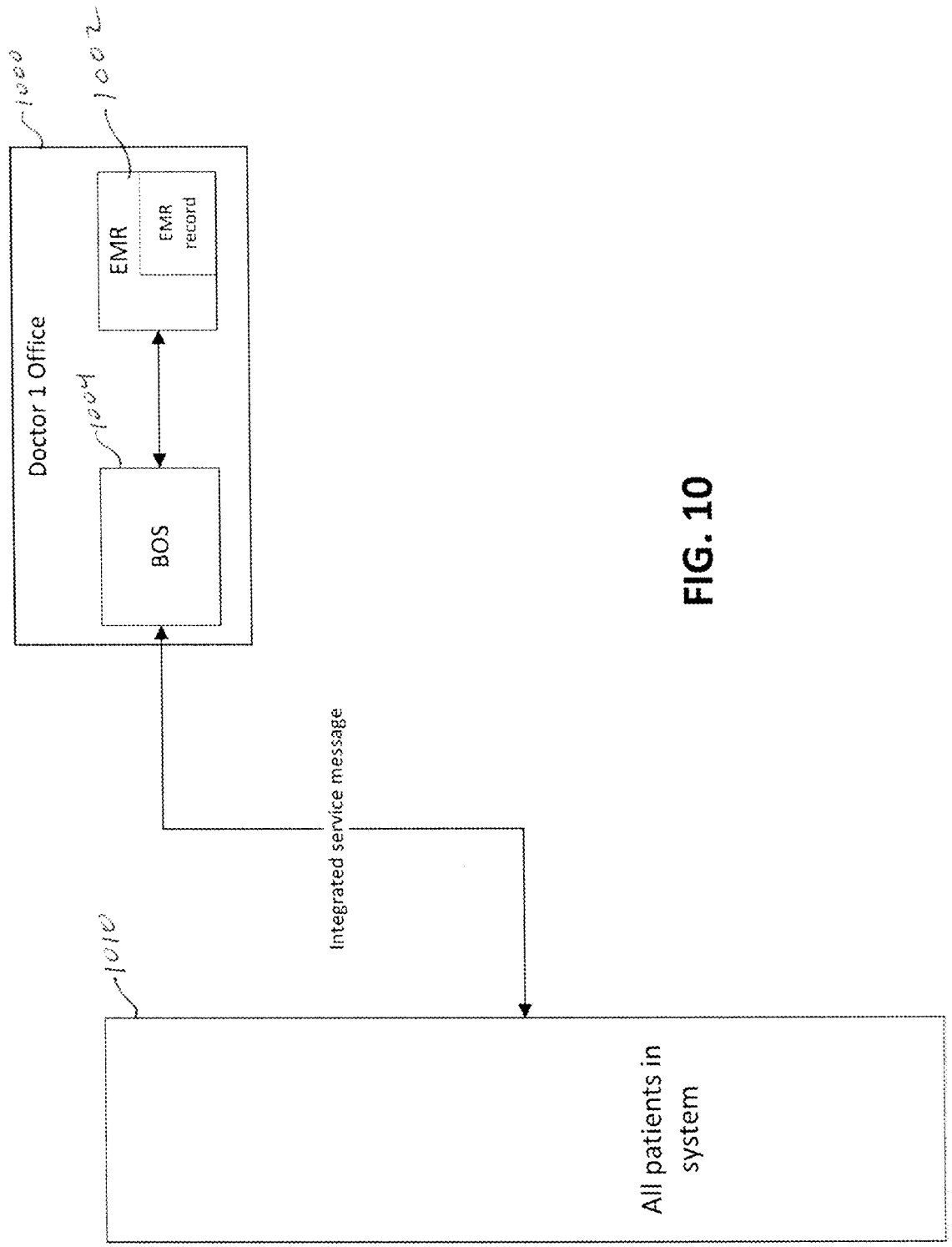
FIGS. 10-14 illustrate a medical data flow according to embodiments of this invention.

FIG. 10 illustrates the database system 1010 and office system 1000 of the first doctor. When a patient visits the first doctor, the patient's PEMR is synchronized via an integrated service message from database 1010 to the local EMR 1002 via the BOS 1004. This transfer causes the updating, namely completing, of an existing corresponding patient's PEMR in the local EMR 1002, or otherwise, the creation of a new EMR record. The first doctor site 1000 then conducts the evaluation, determines the diagnosis, and prescribes the treatment, and the corresponding local EMR 1002 record is updated accordingly. Upon ending the patient visit, the updated EMR record in the local EMR 1002 is transferred via the BOS 1004 to database 1010 using an integrated service message, and the corresponding database 1010 PEMR is made complete. An integrated service message is a transmission format that supports tagged fields for efficient packing and unpacking of message payloads. All data types are supported and integrated. That is, composite types are likewise supported. These data types include but are not limited to: structured, such as those commonly stored in a relational database; semi-structured, such as tagged fields in clinical notes or documents or even complete texts; and unstructured, such as medical image readings. It is within the scope of this invention to optimize the secure transmission of data via the integrated service message, both in terms of, without limitation, security and efficiency, using any known techniques in the art.

Figure 11:
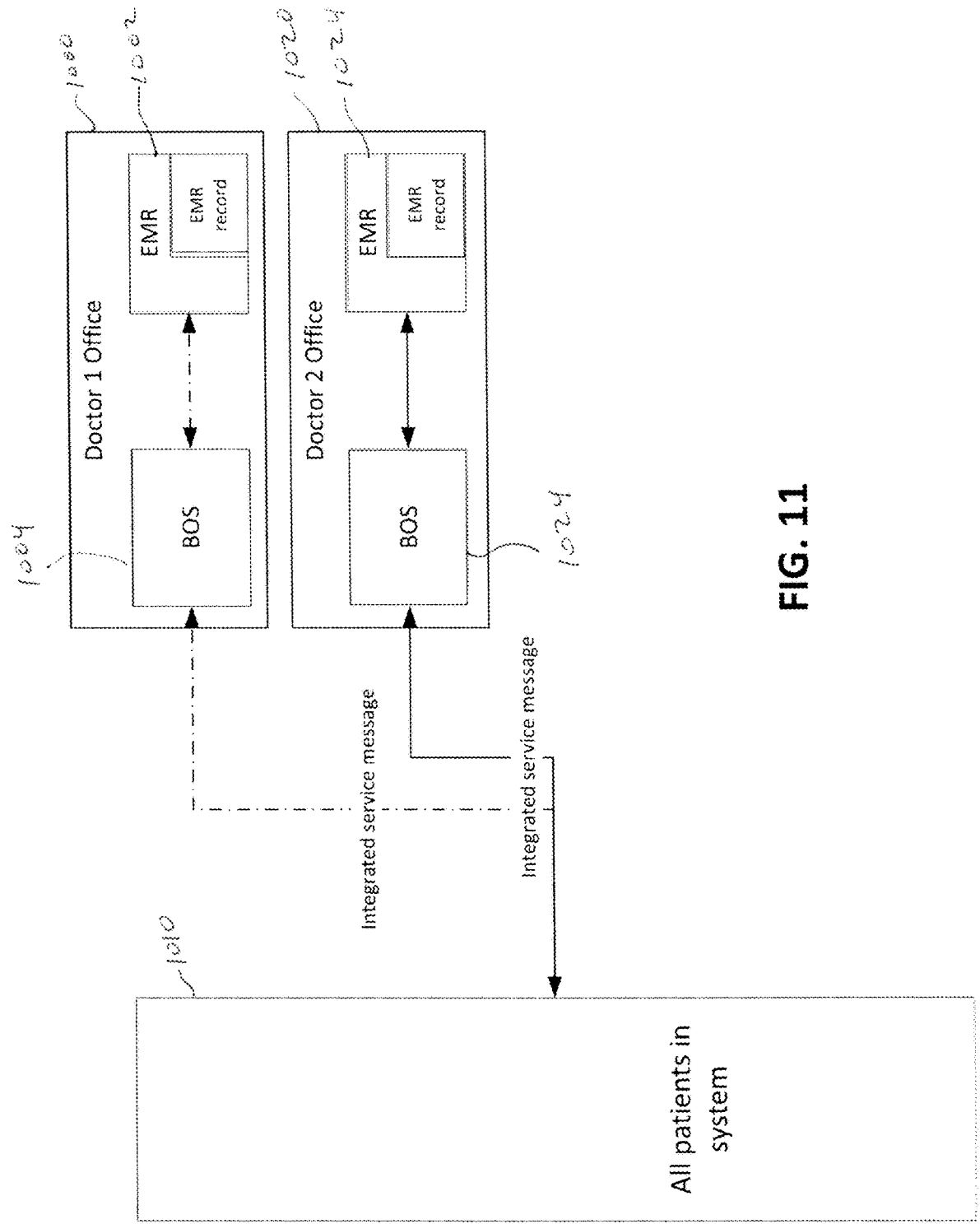

Eventually, the same patient visits a second HCP. FIG. 11 illustrates the secure transfer of that patient's PEMR from database 1010 to a local EMR 1022 using the same process described above. Again, the HCP conducts the evaluation, determines the diagnosis, and prescribes the treatment, and the corresponding local EMR 1022 record is updated accordingly. As aforementioned, upon ending the patient visit at the second doctor site 1020, the updated EMR 1022 is transferred via the BOS 1024 to database 1010 using an integrated service message, and the corresponding database 1010 PEMR is again made complete. Note that patient care at second doctor site 1020 used a complete PEMR. Further, upon completion of the patient's visit, both the local EMR 1022 and database 1010 have a complete copy of the patient's current PEMR; however, the corresponding patient's EMR record within the EMR 1002 at the first doctor site 1000 is no longer current as it does not contain the actions taken during the visit of the second doctor site 1020.

Figure 12:
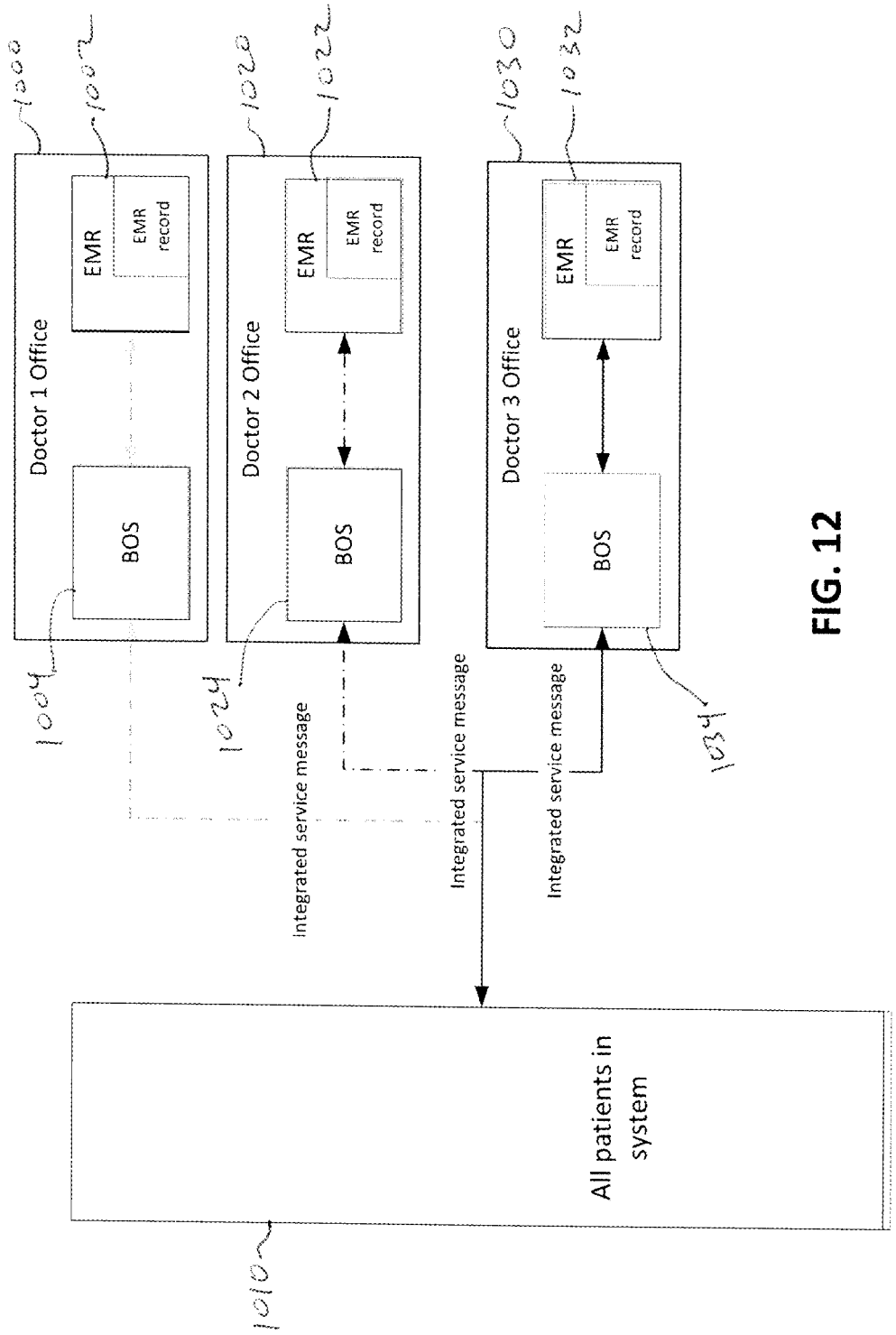

FIG. 12 illustrates the same process; this time, the same patient visits a third HCP, or third doctor site 1030. This visit results in database 1010 and the EMR 1032 at the third doctor site 1030 maintaining a complete PEMR for the patient, but the corresponding patient's EMR record at the EMRs of the first site 1000 and the second site 1020 are no longer current.

Figure 13:
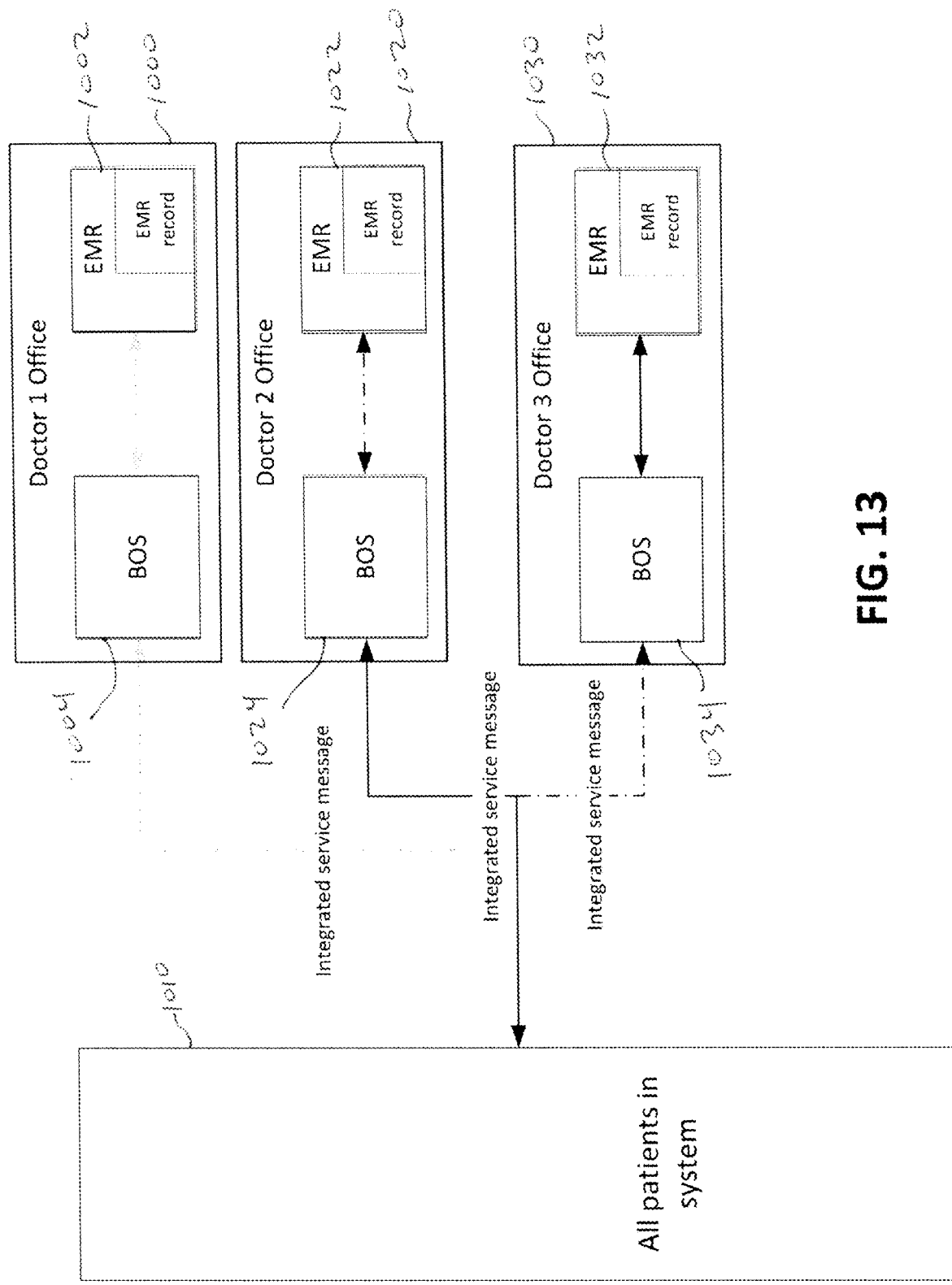
Figure 14:
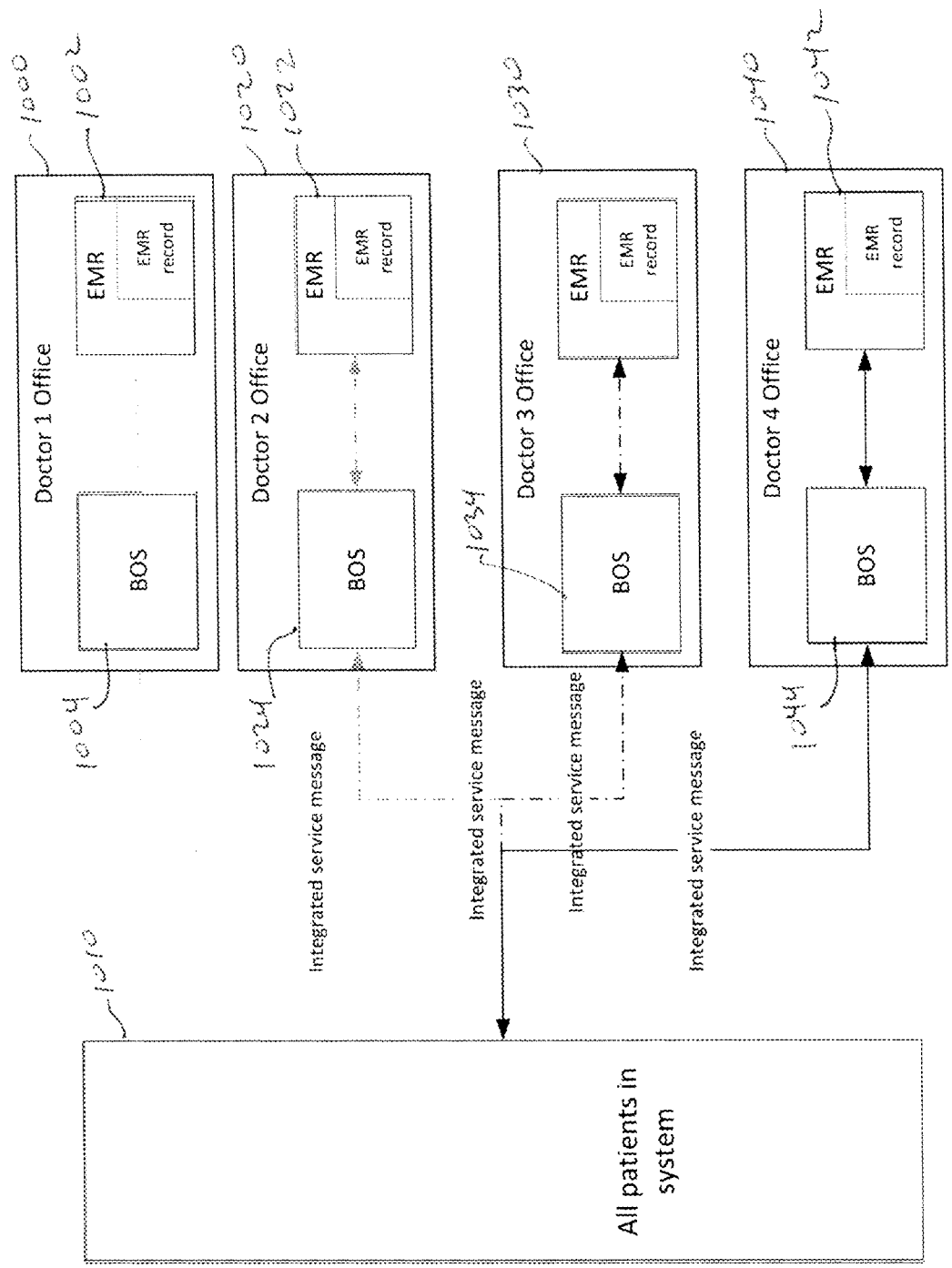

FIG. 13 illustrates the patient returning to the second doctor site 1020. The same data flow processing again transpires. After this visit, the EMR 1022 once again has a complete EMR record at the second doctor site 1020 for the patient, as does database 1010, but the corresponding patient's EMR record at the EMRs of the first site 1000 and the third site 1030 are no longer current. FIG. 14 illustrates the same patient's visit to yet a fourth HCP, or fourth doctor site 1040, with a local EMR 1042 and a BOS 1044.

In embodiments of this invention, all PEMR copies can be synchronized to all EMRs of doctors for the patient using the aforementioned approach by adding synchronization transmissions. Upon completing the processing of an update to a PEMR in database 1010, namely after a completed patient visit at a treating HCP, integrated service messages containing the PEMR for the given patient are sent to all HCPs who have treated the given patient. The list and contact (e.g., EMR location) of treating HCPs is maintained in the PEMR. It is likewise within the scope of this invention to update only a subset of the treating HCPs. The HCPs selected for update can be chosen by the last date of treatment of that patient, the current locality of the patient, or any other selection criteria.

For patient safety and confidentiality, and also for regulation compliances, EMR storage should be secure, using security solutions including but not limited to cryptographic solutions, fragmentation schemes, and block chains. Presently preferred embodiments of this invention include an method that fragments and reassembles data from distributed sites so that no complete copy of the integrated data is stored at a given site; the integrated data record forming the EMR is only reassembled on a mobile device such as a smart phone or on a computer for display while the health-care provider is treating the patient, thus providing the health-care provider a complete patient history. In embodiments of this invention, no actual EMR footprint remains on the provider's viewing device when the record is closed. Thus, using the disclosed approach, patient record storage security is enhanced via fragmentation, while patient treatment safety (supported via the availability of a complete medical history) is provided via temporary defragmentation.

Figure 15:
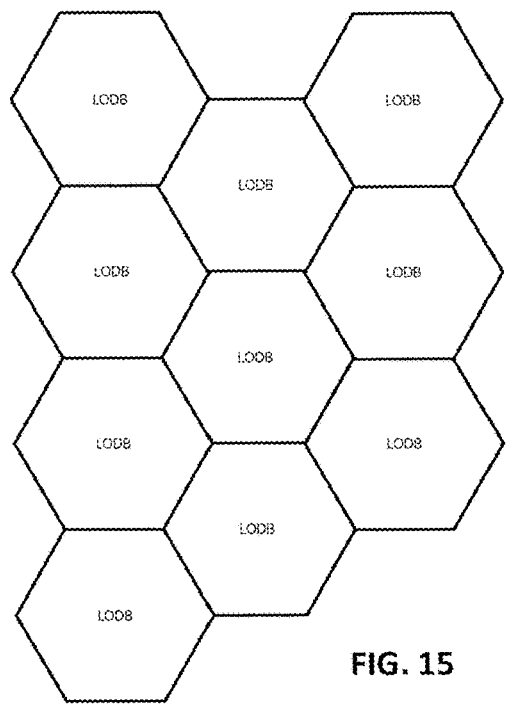
FIG. 15 illustrates a set of electronic medical records (e.g., a set of invaryants).
Figure 16:
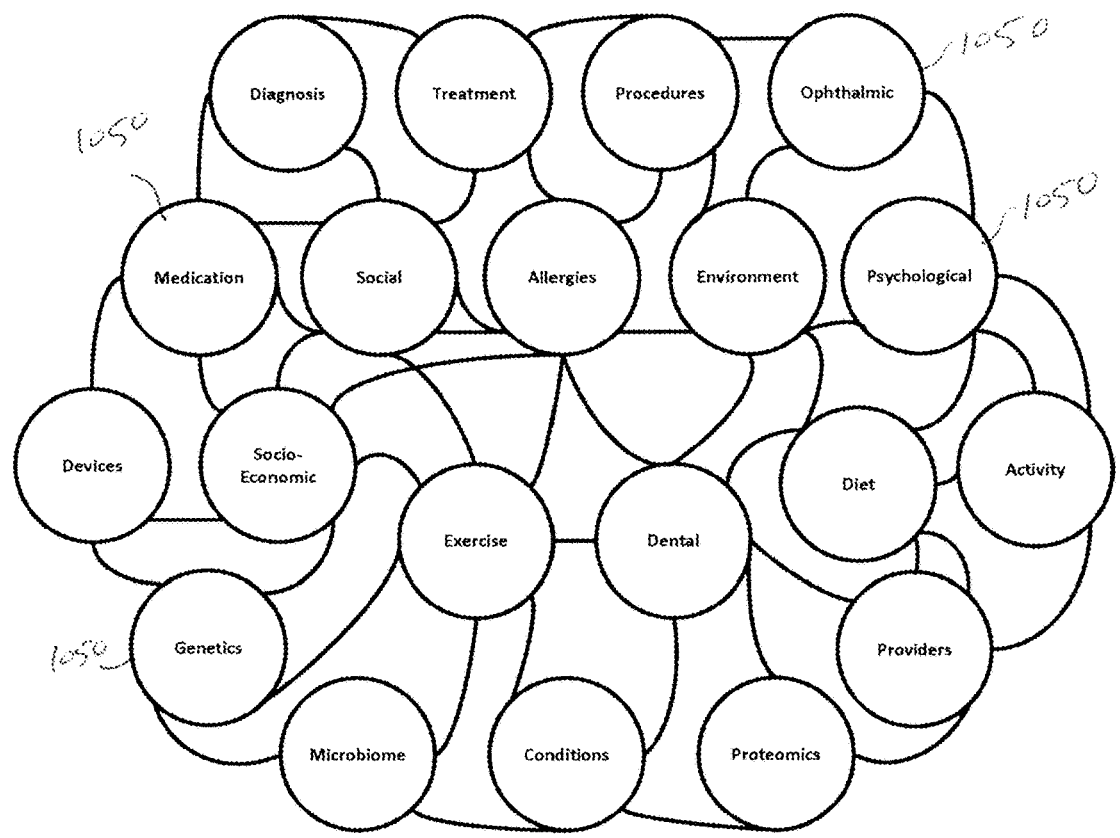
FIG. 16 illustrates high-level objects within a single electronic medical record, comprising components of a PEMR according to embodiments of this invention.

FIG. 15 representatively illustrates a honeycomb-like structure that logically represents an exemplary database of electronic medical records, such as described above, according to embodiments of this invention. Each PEMR according to this invention is desirably a complex record itself comprising of high-level objects representing different aspects of the patient's health and existence. FIG. 16 illustrates some, but not necessarily all, high-level data objects (or simply "objects" herein) 1050 that make up a PEMR according to embodiments of this invention. Not all of the illustrated high-level objects illustrated need be included in any or all of the PEMRs, and additional other high-level patient data objects not illustrated may be included. Also, not all PEMRs will necessarily contain all of the same high-level objects. As shown, a diversity of high-level objects exists, for example some high-level objects relate to physical conditions such as medical conditions, microbiome, genetics, and proteomics; some relate to behaviors such as exercise and activity; some relate to state of mind such as psychological; while still others relate to external inputs such as the environment. Regardless of the type of high-level object, they too are potentially comprised of components, and recursively, potentially themselves also comprised of lower-level components.

Figure 17:
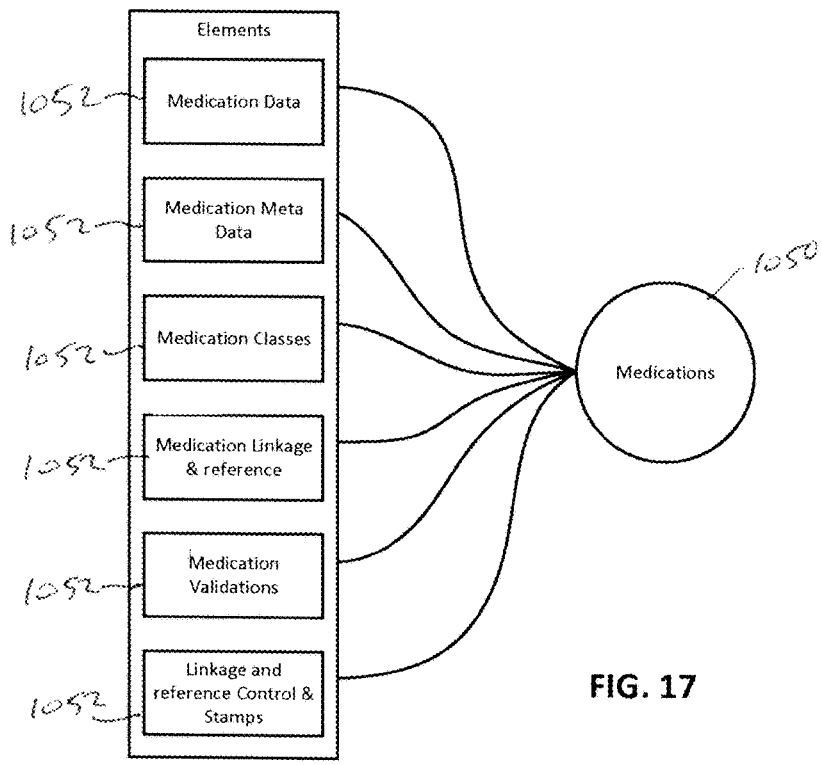
FIG. 17 illustrates exemplary object components comprised within a medication high-level object according to embodiments of this invention.

FIG. 17 illustrates an exemplary object decomposition of a medications high-level object 1050 according to embodiments of this invention. As shown, the medications high-level object 1050 includes data elements 1052, such as but not limited to, medication data, medication metadata, medication classes, medication linkage and reference, medication validations, linkage and reference control and stamps. These data elements include or provide information about the actual medication, what it contains, any associated system or potential known adverse effects, any related or similar medications, etc. Some of the potential data included in the data elements 1052 includes a medications high-level object.

Figure 18:
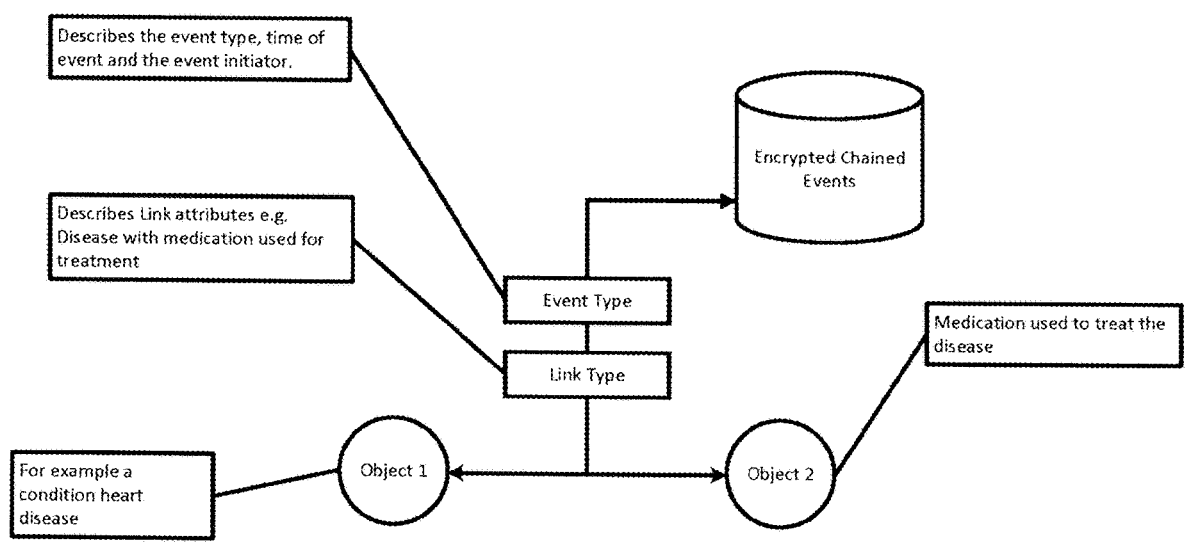
FIG. 18 illustrates exemplary predefined links between objects according to embodiments of this invention.

Diverse sets of links among data objects exist. These links vary in type, in longevity, in importance, and/or in the time of creation. Many of these links are predefined, many of them store associated values, and many of them have default values. FIG. 18 illustrates an exemplary set of links (pre) defined between objects. As shown, Object 1 includes information related to a heart condition. It is linked to Object 2, an object containing information related to medications that treat the heart condition described in Object 1. The link desirably includes attributes describing the medication use, how often the medication is given, the events that precipitated the prescribing of the medication, etc. Furthermore, it is within the scope of this invention that multiple links exists between the objects, namely a set of links; each link within the set can describe a different combination of heart condition ailments and medications corresponding to those ailments. One or more sets of multiple-to-multiple condition-to-medication links can also be provided or included. FIG. 18 further illustrates that the information contained within the objects and within the links is encrypted. The encrypted information can be validated and guaranteed as secure via the use of chained events, such as but not limited to, by block chain implementations.

In embodiments of this invention, no full, integrated copy of any personal electronic medical record is stored on any database. Fragmentation of information according to this invention provides increased data security. Partitioning data across database sites means the data fragments must be defragmented, namely reassembled, and then decrypted to obtain a complete description of the given information. Embodiments of this invention use or incorporate block chains to automatically fragment and/or reassemble the data for security purposes.

Figure 19:
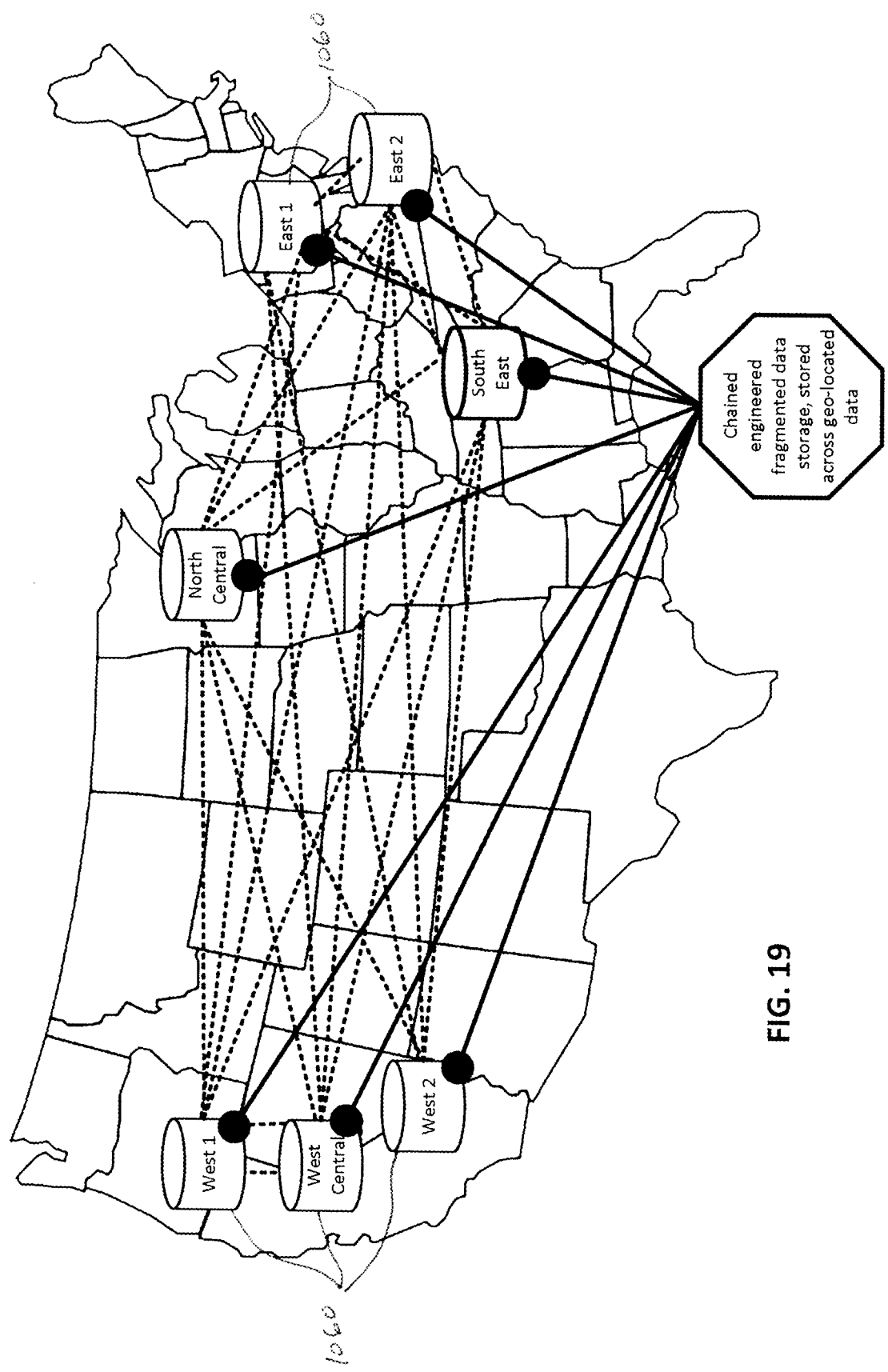
FIG. 19 illustrates exemplary geographic fragmentation of object storage and interrelationships between fragments according to embodiments of this invention.

Additionally or alternatively, the objects can be partitioned across a geographic space. FIG. 19 illustrates objects physically partitioned in databases 1060 across the Continental United States. In FIG. 19, the solid lines represent fragmented data stored across the data center sites 1060, and dashed lines indicate random store/retrieve pathways from chained engineered fragmented data storage. Embodiments of this invention distribute objects across only a random set of data storage sites 1060. The random set selection, potentially based on, but not limited to, a hashing of the object identifier, increases the security as the number of sites 1060 storing the object is not known a priori. For example, assume the availability of seven data centers as shown in FIG. 19. Some objects might be stored across three sites, while others might be stored across only two or potentially all seven sites. More so, clusters of sites might be selected; objects might then be stored across a subset of sites within each or some of these clusters. Clusters might be based on, without loss of generality, vendor (e.g., Azure by Microsoft or AWS by Amazon); likewise clusters might be based on geographic regions, or simply randomly.

Figure 20:
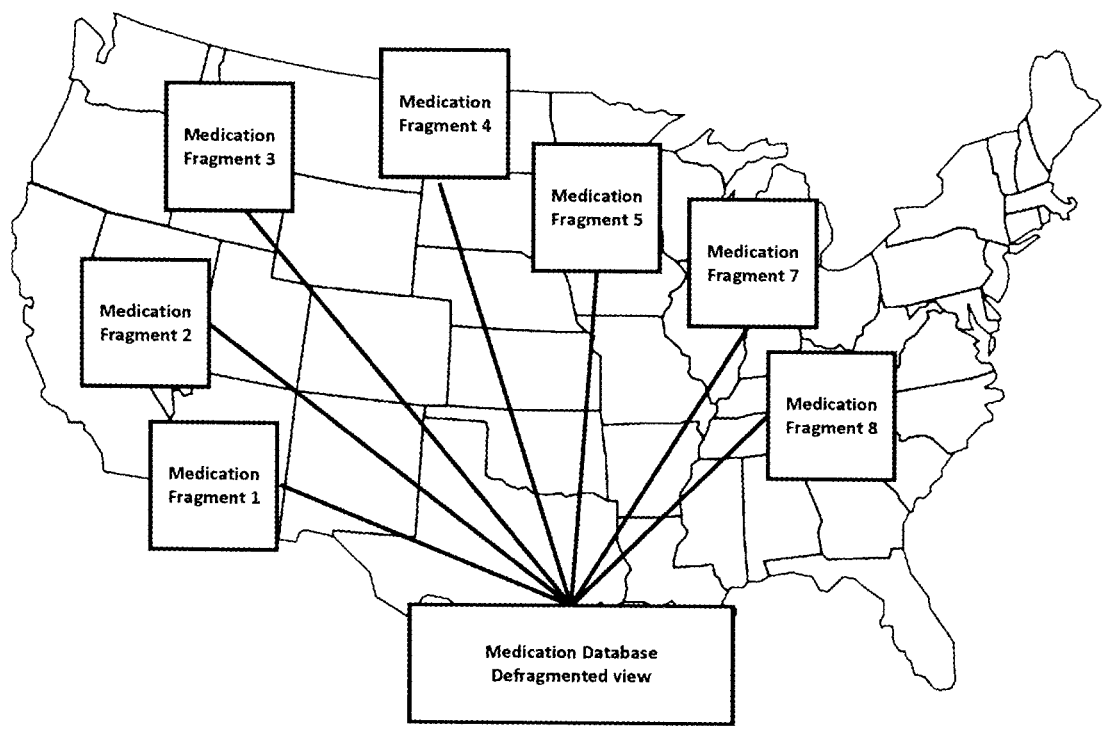
FIG. 20 illustrates exemplary medication specific defragmentation according to embodiments of this invention.
Figure 21:
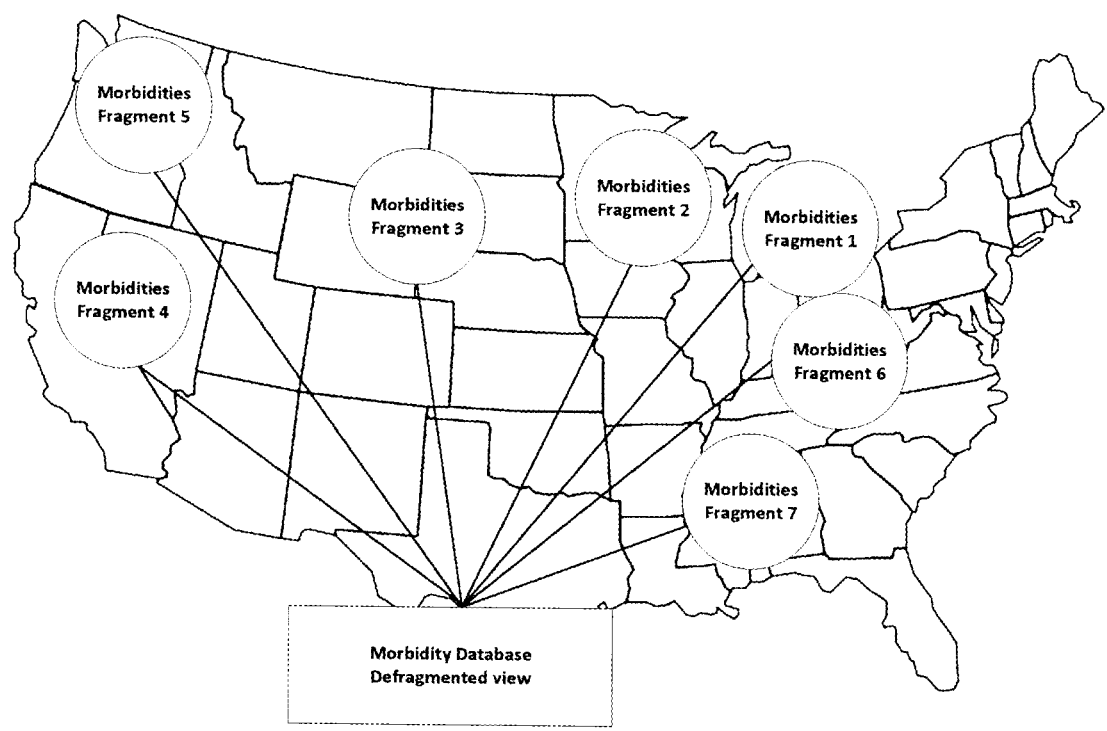
FIG. 21 illustrates exemplary morbidity specific defragmentation according to embodiments of this invention.

Fragmentation in embodiments of this invention is based on a diversity of criteria including but not limited to object type, data value, and/or object interrelationship. As shown in FIGS. 20 and 21, the database is partitioned across the Continental United States according to medication type and morbidity, respectively.

Figure 22:
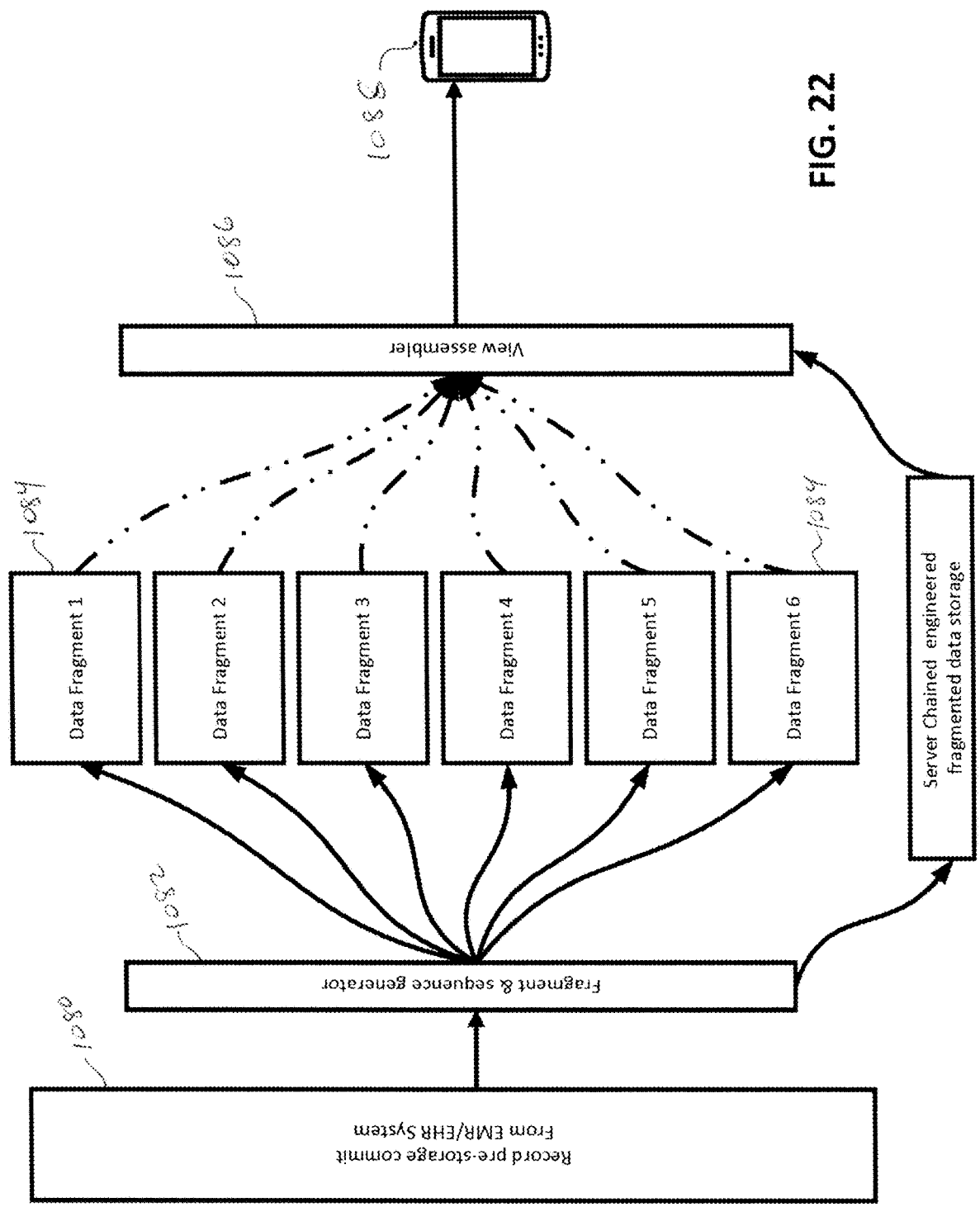
FIG. 22 illustrates secure fragmented storing, loading, and viewing of data, according to embodiments of this invention.

FIG. 22 illustrates automated fragmentation and reconstruction (defragmentation) of objects according to embodiments of this invention. In FIG. 22, records 1080 are initially ingested from their original source, such as the EMR/EHR on the servers discussed above. Any suitable protocol that guarantees a correct and secure transfer of the data from an EMR to the fragmenting engine 1082 can be used. Once ingested, the data are fragmented, and a corresponding sequence generator is attached to each fragment. The fragments 1084 are then allocated to their corresponding sites (e.g., FIG. 19) with a block chain code used to authenticate the data and sequence. In presently preferred embodiments, at no time does any one site have a complete copy of the data, but rather, only a fragment thereof.

Figure 23:
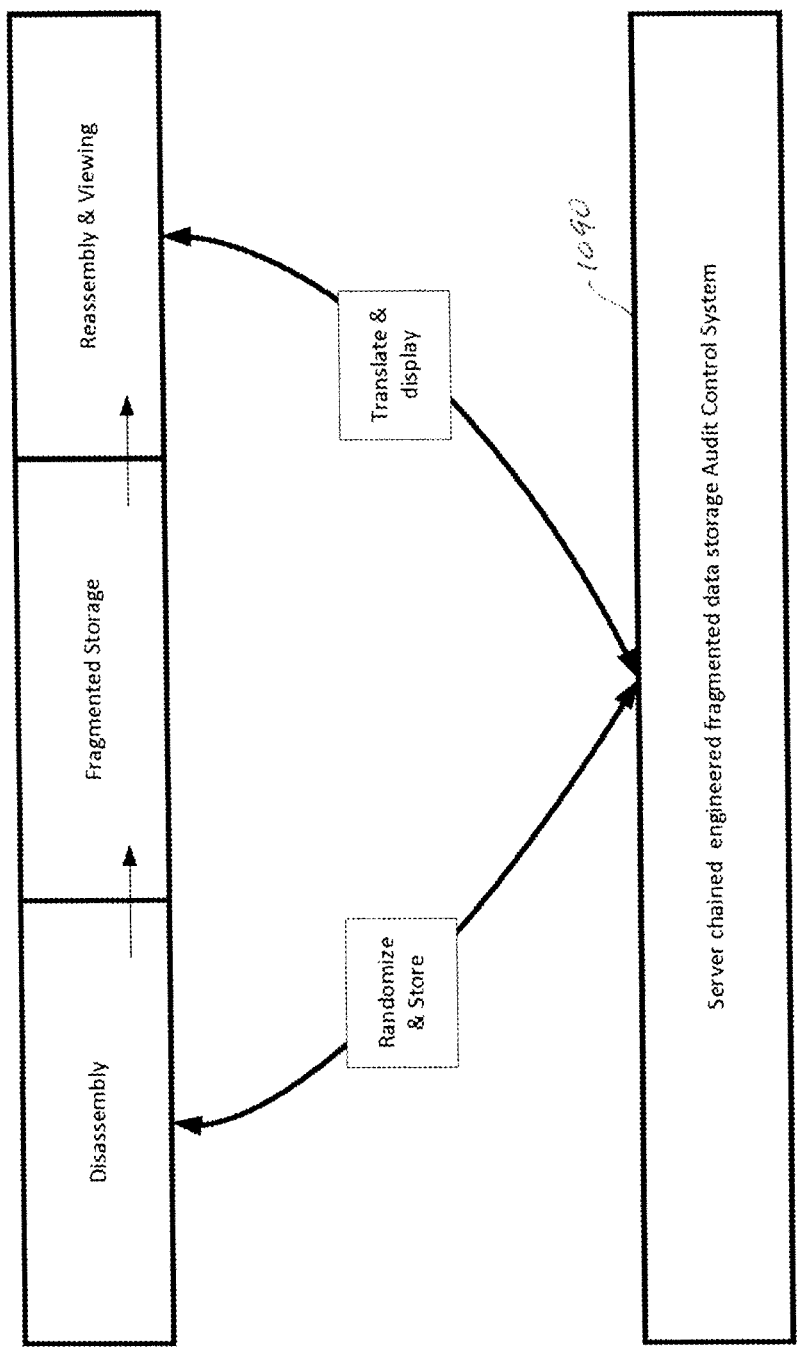
FIG. 23 illustrates the architecture of disassembly, storage, reassembly and viewing of data using secure audit trails, according to embodiments of this invention.

An exemplary disassembly, fragmented storage, and reassembly process is illustrated in FIG. 23. As the record is ingested, it is partitioned into fragments and each fragment is assigned a control sequence number via a block chain server. The assigned sequence number along with the data fragment can be assigned to a geographically dispersed storage site according to the diversity of assignment criteria, as illustrated in, but not limited to, FIGS. 19-21. The block chain sequencing and assignment to storage sites can be accomplished via the use of a central block chain audit control system 1090. Reassembly involves retrieving all the relevant fragments; their location is determined, once again, via interaction with the non-limiting exemplary block chain audit control system 1090. Once retrieved, the fragments, using the sequence number associated with the individual data fragments, are reassembled to form the original record for viewing, such as via view assembler module 1086 on mobile device 1088 in FIG. 22.

For efficiency of care, embodiments of this invention categorize and/or prioritize the defragmentation process, whereby fragment assembly can be organized according to type and/or priority. While all data are relevant, the order by which they are presented is not necessarily of equal importance. For example, if a patient is suffering from a major stroke, data related to a recent dental cleaning is less significant than a cardiologist's report related to a known atrial fibrillation condition or current medications the patient is taking. Thus, the reassembly of data can be prioritized for presentation or display, without loss of generality, based on the symptoms the patient is exhibiting, the specialty of the requesting doctor, the date of the data, etc. This priority can be health-care provider driven or automatically computed.

Returning to FIG. 22 as previously addressed, viewing the original data requires defragmentation, namely reassembling. All corresponding fragments are desirably obtained along with each corresponding sequence number. To do so according to the embodiment of FIG. 22, related fragments are sent temporarily to the viewing device 1088 for use by the health care provider. Such a viewing device includes, without loss of generality, a mobile device such as a smartphone, a limited functionality laptop such as a Chromebook, or a conventional laptop. It is within the scope of this invention to limit the secondary storage available on the viewing device so as to physically prevent any permanent storage of the reconstructed objects. Likewise, it is within the scope of this invention to limit the viewing device to strictly receiving mode; namely, the viewing device will not include a transmission capability; thus, no further transmission is possible. Regardless of the type or configuration of the viewing device 1088, authentication and defragmentation software can be loaded on to the device 1088 to enable temporary PEMR viewing, such as only during actual, active treatment of the patient. As noted earlier, preferably no permanent footprint is created, such that no copy of the PEMR, original or updated, remains on any user component of the computer system of the health care provider upon closing the PEMR after active treatment. Thus, health-care providers can view the actual record but cannot permanently store or share it.

Figure 24:
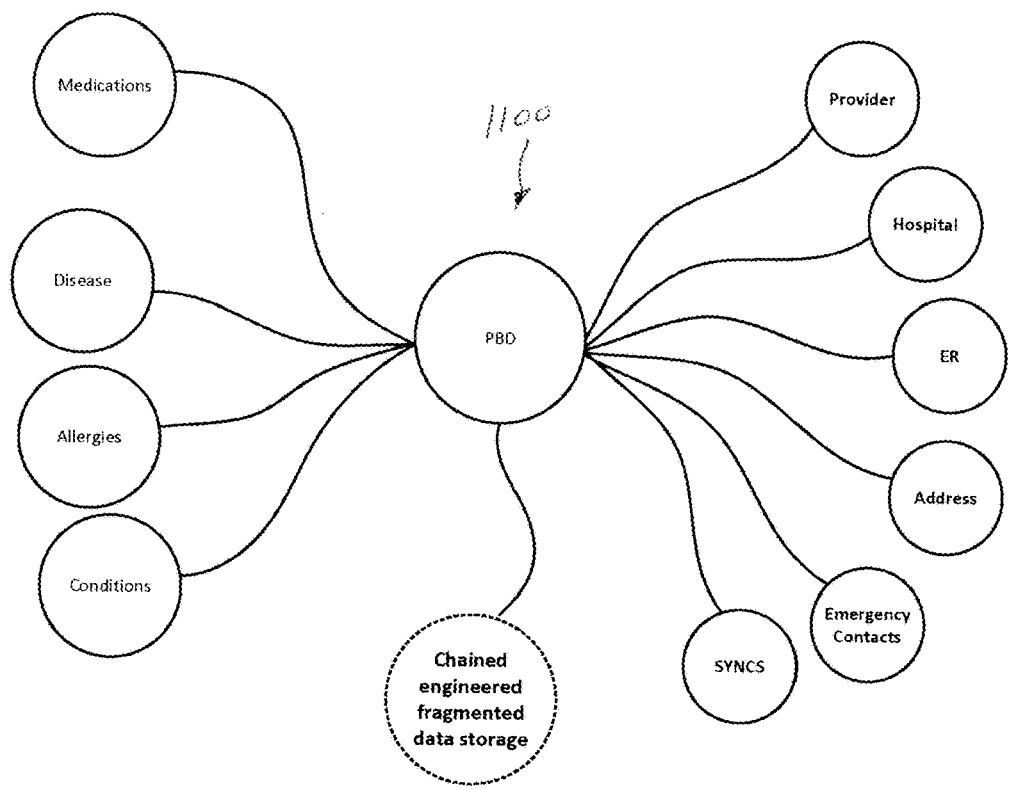
FIG. 24 illustrates a block chain secured exemplary PEMR according to embodiments of this invention.

FIG. 24 illustrates some exemplary components of a PEMR according to embodiments of this invention. It is within the scope of this invention that a PEMR includes only some of or additional objects and predefined links. It is likewise within the scope of the invention that the link itself is an object, potentially a composite object. As shown, an exemplary PEMR 1100 includes medications taken, diseases encountered, known patient allergies, conditions suffered, providers used, hospitals and ERs visited, and various personal data such as home and work addresses and emergency contacts. FIG. 24 is a logical illustration, as the actual data are desirably fragmented across multiple geographical sites as described above. Furthermore, the authentication of the data is desirably maintained via the use of block chains.

Figure 25:
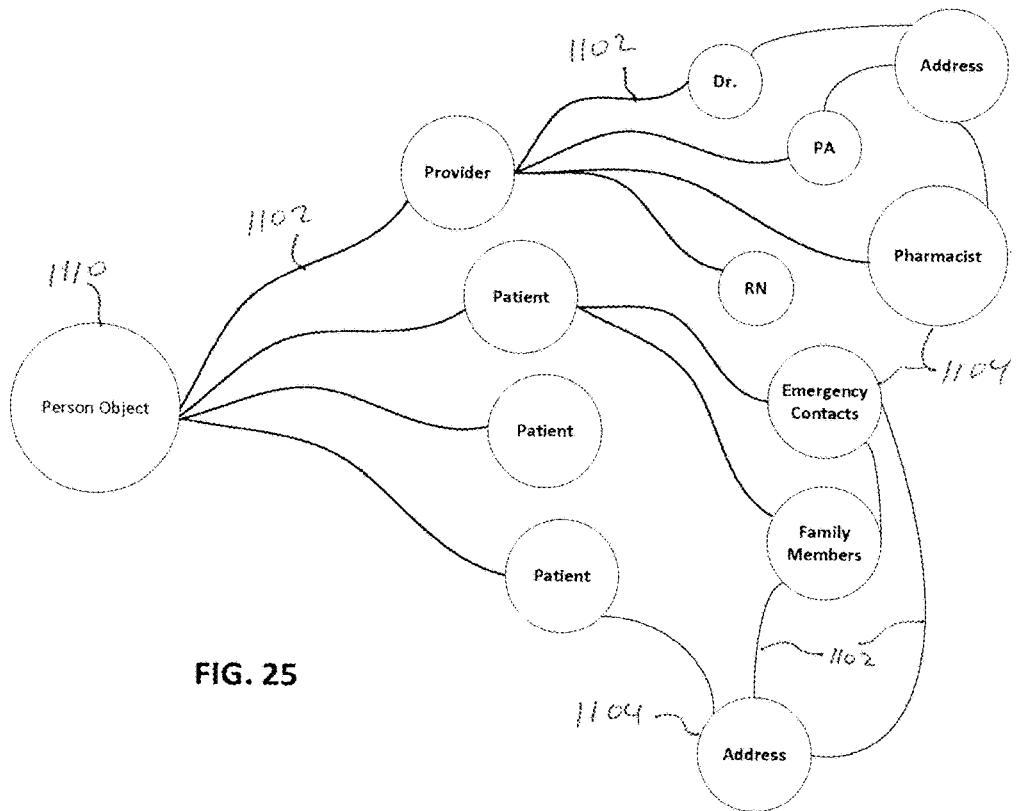
FIG. 25 illustrates exemplary interactions of objects according to embodiments of this invention.

Having built a PEMR, authorized and authenticated health-care providers, both traditional such as a medical doctor, physician's assistant, or registered nurse, or non-traditional, such as designated family members or friends, spiritual counselors, or dietary food providers, can access the records to provide informed actions. As shown in FIG. 25, links 1102, both predefined and learned, are used to designate the interaction between various objects 1104. These links 1102 include those that are associated with objects that make up the individual PEMR 1110, but also potentially those that define the role of those accessing the PEMR. In embodiments of this invention, Role Based Access Control (RBAC) as well as on refined constraint RBAC schemes as disclosed in Frieder, et al., "Refined Permission Constraints Using Internal and External Data Extraction in a Role-Based Access Control System," U.S. Pat. No. 8,271,527, can be used to constrain the access of each party accessing the PEMR 1110. Note that as shown in FIG. 25, the entire person object PEMR 1110 comprises of many links of varying types.

Thus the invention provides a method and system for storing personal medical histories and sharing the history records between and across multiple health-care providers. The method and system provides sufficient security measures to protect the sensitive personal information while providing improved information for active treatment by a health-care provider.

It will be apparent to those skilled in the art that various modifications and variations can be made in the present disclosure without departing from the scope or spirit of the disclosure. Other aspects of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A method of consolidating and synchronizing medical history for a patient, comprising:
   automatically fragmenting a personal electronic medical record for the patient into a plurality of data fragments;
   storing the plurality of data fragments distributed across one or more databases;
   reassembling the plurality of data fragments for display of the personal electronic medical record via a computer system of a health-care provider upon the patient checking-in for a patient appointment at the health-care provider;
   updating the personal electronic medical record with data from the health-care provider to form an updated personal electronic medical record for the patient, wherein the updated personal electronic medical record replaces the personal electronic medical record for the storing across the one or more databases;
   upon the patient checking-out for the patient appointment at the health-care provider, automatically fragmenting the updated personal electronic medical record for the patient into a second plurality of data fragments for storage across the one or more databases; and
   upon the patient checking-out for the patient appointment at the health-care provider the updated personal electronic medical record closing on the computer system of the health-care provider, wherein the reassembling only occurs during active treatment of the patient by the health-care provider during the patient appointment at the health-care provider, and no copy of the personal electronic medical record or the updated personal electronic medical record remains on any user component of the computer system of the health care provider upon closing of the updated personal electronic medical record at the checking-out; and
   storing the second plurality of data fragments distributed across the one or more databases in place of the plurality of data fragments across the one or more databases.

2. The method of claim 1, wherein no integrated copy of the personal electronic medical record is stored on the one or more databases.

3. The method of claim 1, wherein the personal electronic medical record for the patient comprises a corresponding authenticator assigned to the patient to allow access to the personal electronic medical record by the health-care provider.

4. The method of claim 1, further comprising randomly distributing the data fragments across the one or more databases.

5. The method of claim 1, further comprising distributing the data fragments across a plurality of geographically distributed databases.

6. The method of claim 1, further comprising automatically attaching a sequence generator to each of the plurality of data fragments and the second plurality of data fragments for reassembling.

7. The method of claim 6, wherein a block chain code authenticates the data fragments and sequence for reassembling.

8. The method of claim 1, further comprising assigning a control sequence number to each of the plurality of data fragments and the second plurality of data fragments via a block chain server for reassembling.

9. The method of claim 1, further comprising categorizing and/or prioritizing the plurality of data fragments for reassembly and display of relevant health information as a function of a specialty of the health-care provider.

10. The method of claim 1, further comprising displaying the reassembled personal electronic medical record on a viewing device of the health-care provider, wherein reassembled electronic medical record is not capable of being stored on or forwarded from the viewing device.

11. The method of claim 1, further comprising transferring the plurality of data fragments to a local electronic medical record of the health-care provider via an integrated service message.

12. The method of claim 1, wherein a cloud based data server performs the automatically fragmenting, storing, and reassembling of the personal electronic medical record.

13. The method of claim 1, wherein the plurality of data fragments is stored as distributed data fragment objects, reassembling the plurality of data fragments comprises automatically synchronizing the distributed data fragment objects in a local electronic medical record of the health-care provider, and the updated personal electronic medical record for the patient is stored as a second plurality of distributed data fragment objects until requested by the first health-care provider or a second health-care provider.

14. The method of claim 13, further comprising:
receiving a second request for the personal electronic medical record by the second health-care provider treating the patient;
automatically reassembling the distributed second plurality of data fragment objects in a second local electronic medical record of the second health-care provider;
transferring a further updated personal electronic medical record from the second health-care provider to the cloud based data server for distributed storage.

15. The method of claim 14, further comprising:
randomly distributing the data fragment objects across the one or more databases; and
automatically attaching a sequence generator to each of the distributed data fragment objects for reassembling, wherein the personal electronic health record for the patient comprises a corresponding authenticator assigned to the patient to allow access to the personal electronic medical record by the health-care provider, and a block chain code authenticates the distributed data fragment objects and sequence for reassembling.

16. The method of claim 1, wherein the method is applied to a plurality of personal electronic medical records of a plurality of patients, and further comprising:
automatically fragmenting each of the personal electronic medical records into the plurality of data fragments, via the cloud based data server;
distributing the data fragments across a plurality of geographically distributed databases, wherein the data fragments for the each of the personal electronic medical records are distributed across at least two different combinations of the geographically distributed databases.

17. The method of claim 2, further comprising:
providing a mobile device of the patient with an authenticator for allowing access to the plurality of data fragments distributed across the one or more databases, wherein the authenticator is a computer-readable indicia;
the authenticator is provided to the health-care provider server apparatus from the mobile device of the patient upon the patient checking-in at the health-care provider, and the authenticator is automatically transmitted to a remote server apparatus to authorize access to the personal electronic medical record, wherein the reassembling only occurs during the active treatment of the patient by the health-care provider.

18. The method of claim 17, further comprising:
providing the authenticator to the health-care provider for the checking-in for the patient appointment;
providing the authenticator to the health-care provider a second time at the checking-out of the patient appointment;
receiving electronic permission from the patient for the updating the personal electronic medical record at the checking-out.

19. The method of claim 18, further comprising:
the patient providing the authenticator to a second server apparatus of a second health-care provider from the mobile device of the patient upon the patient checking-in for a second patient appointment at the second health-care provider, and
automatically transmitting the authenticator from the second server apparatus to the remote server apparatus to authorize access by the second server apparatus to the updated personal electronic medical record.

20. The method of claim 1, further comprising:
reassembling the second plurality of data fragments for display of the updated personal electronic medical record via a second computer system of a second health-care provider upon the patient checking-in for a second patient appointment at the second health-care provider;
further updating the personal electronic medical record with further data from the second health-care provider to form a second updated personal electronic medical record for the patient, wherein the second updated personal electronic medical record replaces the updated personal electronic medical record for the storing across the one or more databases;
upon the patient checking-out for the second patient appointment at the second health-care provider, automatically fragmenting the second updated personal electronic medical record for the patient into a third plurality of data fragments for storage across the one or more databases; and
upon the patient checking-out for the second appointment at the second health-care provider the second updated personal electronic medical record closing on the second computer system of the second health-care provider, wherein the reassembling the second plurality of data fragments only occurs during a second active treatment of the patient by the second health-care provider during the second appointment at the second health-care provider, and no copy of the updated personal electronic medical record or the second updated personal electronic medical record remains on any further user component of the second computer system of the second health care provider upon closing of the third updated personal electronic medical record at the checking-out; and
storing the third plurality of data fragments distributed across the one or more databases in place of the second plurality of data fragments across the one or more databases.

21. The method of claim 20, wherein the second updated personal electronic medical record for the patient is stored as the third plurality of distributed data fragment objects until requested again by the first health-care provider or the second health-care provider.

22. The method of claim 21, wherein each of the checking-in and checking-out for the first patient appointment and the second patient appointment comprises the patient showing the first or second health-care provider a mobile device with a computer-readable authenticator for the patient.

* * * * *